United States Patent
Hayashida

(10) Patent No.: US 10,711,307 B2
(45) Date of Patent: Jul. 14, 2020

(54) METHOD FOR DETERMINING STATE OF DIFFERENTIATION OF STEM CELLS, AND NOVEL DIFFERENTIATION MARKER USED THEREFOR

(71) Applicant: FUJIFILM WAKO PURE CHEMICAL CORPORATION, Osaka-shi, Osaka (JP)

(72) Inventor: Yukinobu Hayashida, Amagasaki (JP)

(73) Assignee: FUJIFILM WAKO PURE CHEMICAL CORPORATION, Osaka (JP)

( * ) Notice: Subject to any disclaimer, the term of this patent is extended or adjusted under 35 U.S.C. 154(b) by 557 days.

(21) Appl. No.: 15/501,761

(22) PCT Filed: Aug. 19, 2015

(86) PCT No.: PCT/JP2015/073281
§ 371 (c)(1),
(2) Date: Feb. 3, 2017

(87) PCT Pub. No.: WO2016/027842
PCT Pub. Date: Feb. 25, 2016

(65) Prior Publication Data
US 2017/0342490 A1    Nov. 30, 2017

(30) Foreign Application Priority Data
Aug. 20, 2014    (JP) .................................. 2014-167800

(51) Int. Cl.
| | | |
|---|---|---|
| *C12Q 1/68* | (2018.01) | |
| *C12P 19/34* | (2006.01) | |
| *C12Q 1/6881* | (2018.01) | |
| *G01N 33/50* | (2006.01) | |
| *G01N 33/68* | (2006.01) | |
| *C12N 15/09* | (2006.01) | |
| *C07K 14/47* | (2006.01) | |

(52) U.S. Cl.
CPC ........ *C12Q 1/6881* (2013.01); *C07K 14/4702* (2013.01); *C12N 15/09* (2013.01); *G01N 33/50* (2013.01); *G01N 33/5073* (2013.01); *G01N 33/68* (2013.01); *C12Q 2600/156* (2013.01); *C12Q 2600/158* (2013.01)

(58) Field of Classification Search
CPC .. C12Q 2600/158; C12Q 1/6881; C12Q 1/68; C12Q 1/6853; C12Q 1/686; G01N 33/50; G01N 33/5073; G01N 33/68
See application file for complete search history.

(56) References Cited

U.S. PATENT DOCUMENTS

2011/0250589 A1    10/2011   Lama
2013/0017570 A1     1/2013   Ohashi

FOREIGN PATENT DOCUMENTS

| WO | WO 2011/091270 A2 | 7/2011 |
| WO | WO 2011/101550 A1 | 8/2011 |
| WO | WO 2013/151670 A2 | 10/2013 |

OTHER PUBLICATIONS

GenBank Locus X92591, M.musculus mRNA for fkh-4 protein, Apr. 18, 2005, from https://www.ncbi.nlm.nih.gov (Year: 2005).*
GenBank Locus NM 001013735, Homo sapiens forkhead box B2 (FOXB2), mRNA, Feb. 21, 2014, from https://www.ncbi.nlm.nih.gov (Year: 2014).*
Yang, R. et al. Generation of folliculogenic human epithelial stem cells from induced pluripotent stem cells, Published Jan. 28, 2014, Nat. Comm. 5:3071 doi: 10.1038/ ncomms4071 (2014). (Year: 2014).*
Larsson, H.M. et al. "Sorting Live Stem Cells Based on Sox2 mRNA Expression", PLoS One. Nov. 2012; 7(11):pp. 1-8. (Year: 2012).*
Van Roon et al., "BRAF mutation-specific promoter methylation of FOX genes in colorectal cancer," *Clinical Epigenetics*, 5: 2 (2013).
Japanese Patent Office, International Search Report in International Patent Application No. PCT/JP2015/073281 (Nov. 17, 2015).
Japanese Patent Office, International Preliminary Report on Patentability in International Patent Application No. PCT/JP2015/073281 (Mar. 2, 2017).
Anonymous, "EM_STD:X92591" (Apr. 25, 1996) [obtained at: http://ibis.internal.epo.org/exam/dbfetch.jsp?id=EM_STD:X92591 on Dec. 7, 2017].

(Continued)

*Primary Examiner* — Stephen T Kapushoc
(74) *Attorney, Agent, or Firm* — Leydig, Voit & Mayer, Ltd.

(57) ABSTRACT

The invention relates to a method which is capable of determining, at an initial stage of differentiation, the differentiated state of undifferentiated stem cells. The invention provides a method for determining a differentiated state of a cell comprising detecting expression of FOXB2 gene of a stem cell, and determining the differentiated state based on the result, and a differentiation marker selected from mRNA or protein derived from the FOXB2 gene. The invention is applicable to quality management of the stem cells or to methods for preparation and isolation of the differentiated cells. Further, because the differentiated cells can be determined at an initial stage of culture, the invention is useful for an early stage screening of cells and for quality management of the stem cells, and reduction in culturing period and cost reduction in expenditure regarding a culture medium, or the like, can be expected.

13 Claims, 5 Drawing Sheets
Specification includes a Sequence Listing.

(56) References Cited

OTHER PUBLICATIONS

Anonmymous, "UPI0000025CF8" (Jan. 1, 2009) [obtained at: http://uniprot.org/uniparc/UP10000025CF8 on Dec. 7, 2017].
Pohl et al., "Sequence and expression of FoxB2 (XFD-5) and Foxl1c (XFD-10) in *Xenopus embryogenesis*," Mech. Dev., 117(1-2): 283-287 (2002).
Pohl et al., "Of Fox and Frogs: Fox (fork head/winged helix) transcription factors in *Xenopus* development," Gene, 344: 21-32 (2005).
European Patent Office, Extended European Search Report in European Patent Application No. 15833859.0 (dated Dec. 20, 2017).

* cited by examiner

[Fig. 1]
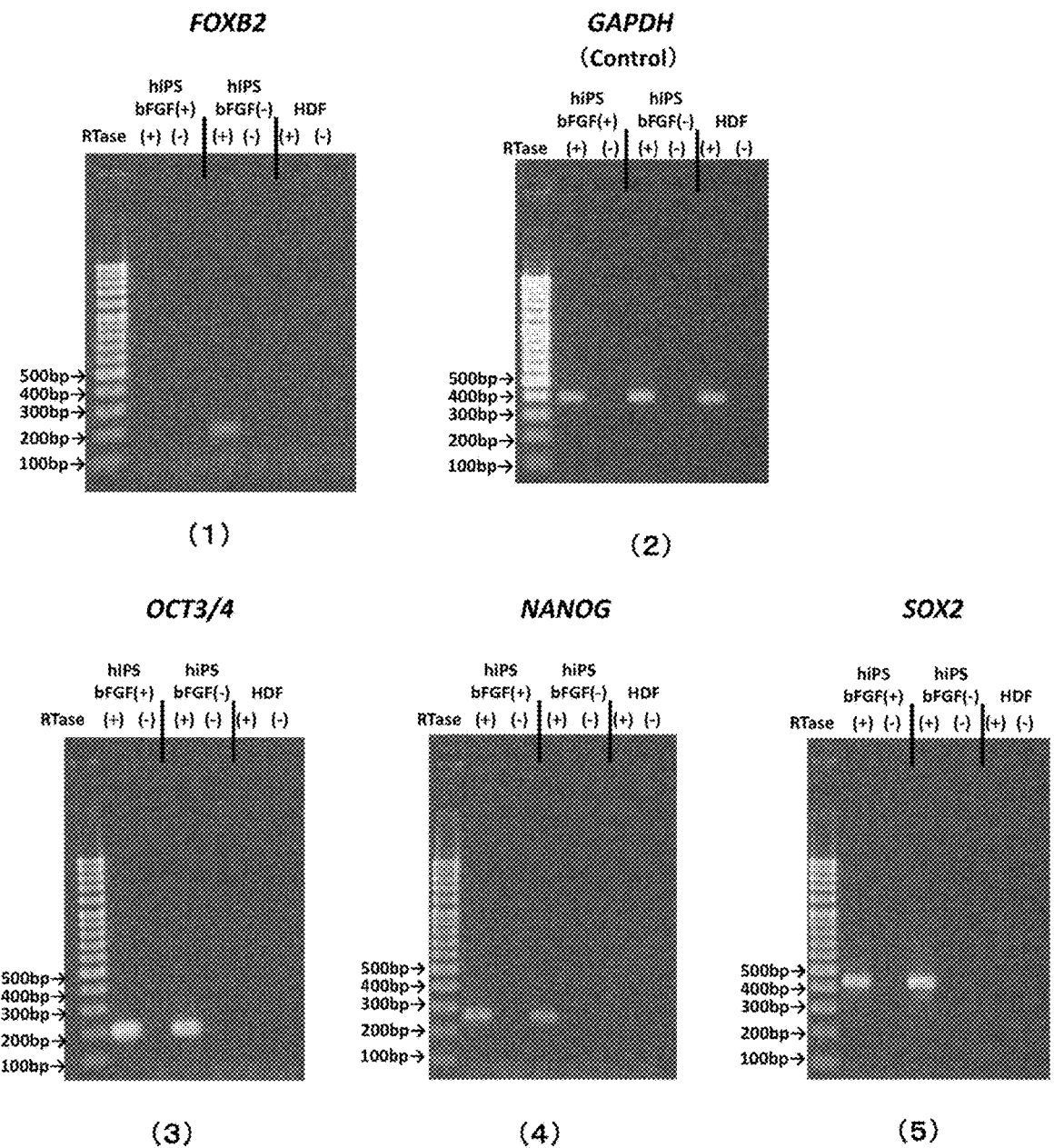

[Fig. 2]
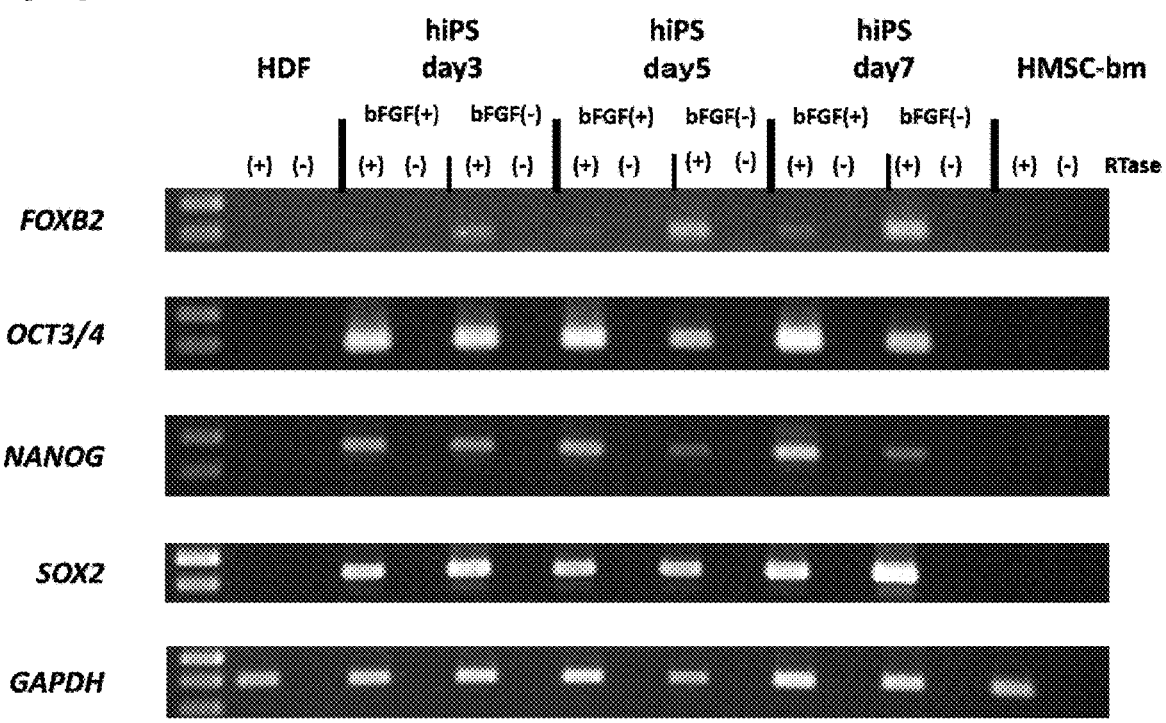

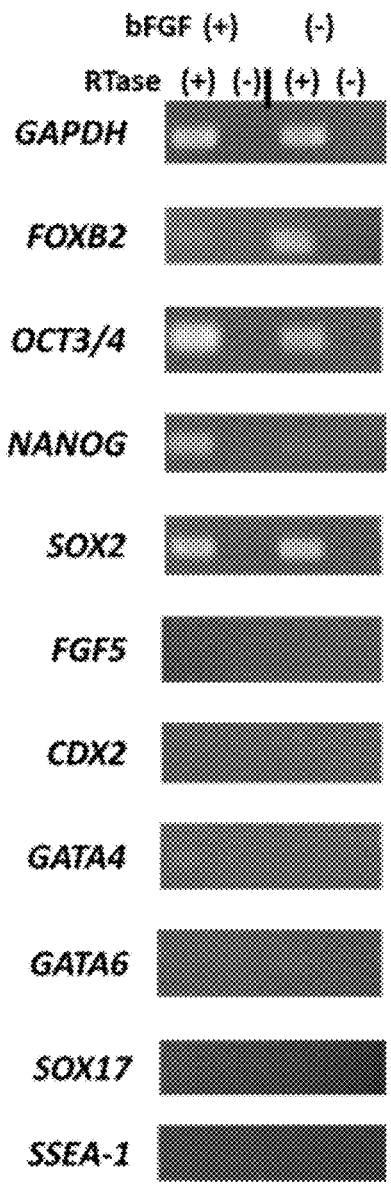
[Fig. 3]

[Fig. 4]
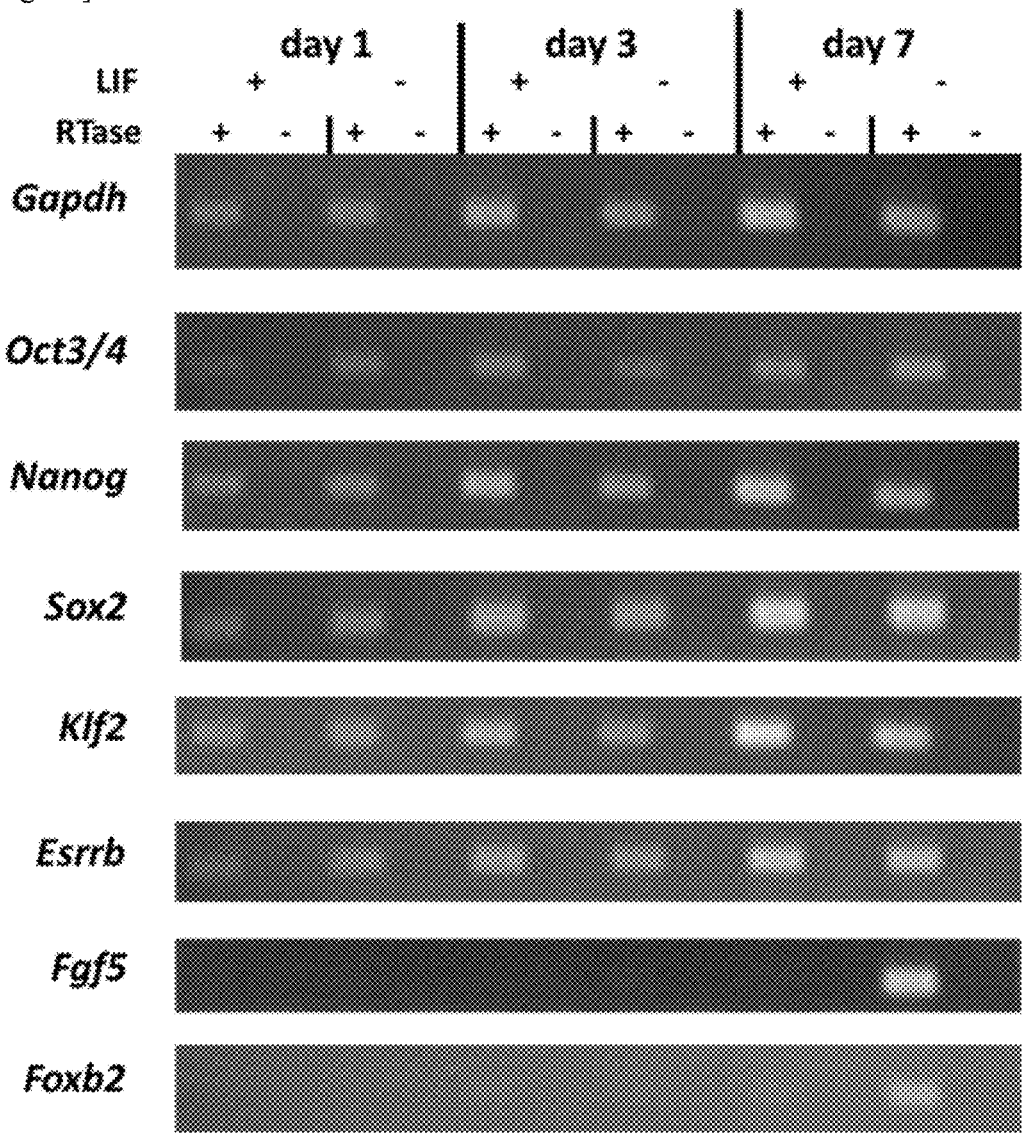

[Fig. 5]
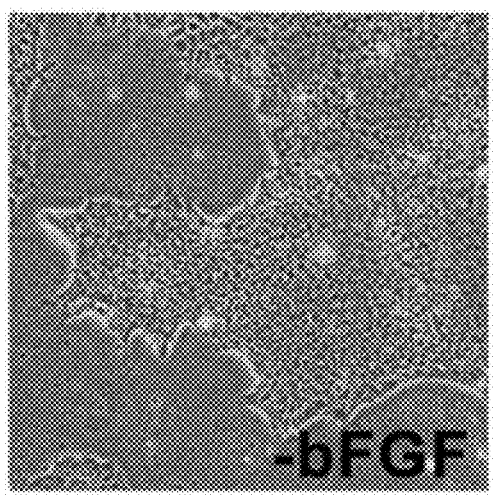
(1)
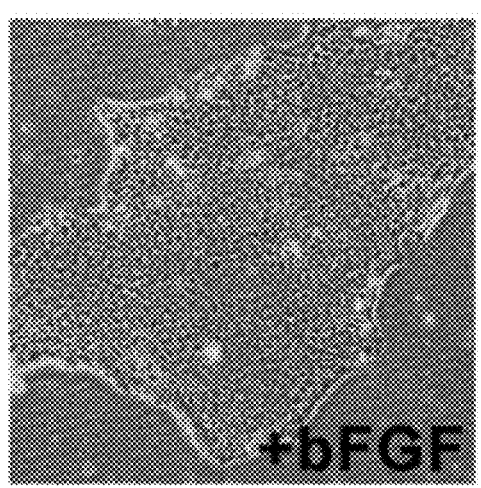
(2)

METHOD FOR DETERMINING STATE OF DIFFERENTIATION OF STEM CELLS, AND NOVEL DIFFERENTIATION MARKER USED THEREFOR

CROSS-REFERENCE TO RELATED APPLICATIONS

This patent application is the U.S. national phase of International Patent Application No. PCT/JP2015/073281, filed Aug. 19, 2015, which claims the benefit of Japanese Patent Application No. 2014-167800, filed on Aug. 20, 2014, which are incorporated by reference in their entireties herein.

INCORPORATION-BY-REFERENCE OF MATERIAL ELECTRONICALLY SUBMITTED

Incorporated by reference in its entirety herein is a computer-readable nucleotide/amino acid sequence listing submitted concurrently herewith and identified as follows: 31,907 bytes ASCII (Text) file named "727736Replacement-SequenceListing.txt," created Jul. 31, 2017.

TECHNICAL FIELD

The present invention relates to a novel differentiation marker which is capable of determining the differentiated state of a stem cell at an early stage of differentiation.

BACKGROUND ART

Pluripotent stem cells such as ES cells (embryonic stem cells) or iPS cells (induced pluripotent stem cells) require such technique, for example, that they are to be co-cultured with feeder cells, to be cultured in a conditioned medium (CM) derived from feeder cells, or the addition of basic FGF (bFGF/FGF2, basic fibroblast growth factor) or LIF (leukemia inhibitory factor), or the like, in order to maintain pluripotency thereof. Otherwise, they will lose pluripotency caused by environment and condition of cells, and they may be sometimes easily differentiated. Therefore, it is important to know exactly an undifferentiated state (a state having pluripotency) or the differentiated state of the stem cells.

In the field of regenerative medicines, the pluripotent stem cells are transplanted after being differentiated into cells of interest. However, when the undifferentiated cells are mixed in the cells to be transplanted, there is risk that they may cause oncogenesis. Therefore, technique of determining whether the undifferentiated stem cells are mixed in the pluripotent stem cells that have been subjected to differentiation-inducing treatment is important.

However, it is difficult to determine the differentiated state of the cells by cell appearance.

Therefore, as a method for determining the differentiated state of the pluripotent stem cells, a method for detecting markers which indicates the differentiated state has been carried out. For example, as pluripotency markers of the pluripotent stem cells, an alkaline phosphatase, Nanog, Oct4, TRA-1-60, Sox, LIF-R, and the like have been known. Since the pluripotent stem cells express these markers in the undifferentiated state, it is capable of determining whether the stem cells have maintained the undifferentiated state by detection of these markers. However, these markers are not capable of determining a differentiated state unless the stem cells are differentiated to a certain degree (for example, to any of three germ layers). Therefore, it is difficult to determine at an early stage of differentiation after induction of differentiation, whether the undifferentiated cells maintain the undifferentiated state (pluripotency), or whether it is in a state where differentiation potential to differentiate in the future has been acquired.

On the other hand, a group of transcription factors with a fork head or a winged-helix DNA-binding domain which is referred to as Fox (Forkhead box) has been known (Non-Patent Literature 1), and about 50 kinds are known to be present in human (FOXB1, FOXB2, or the like). Although a protein expressed by Fox has been known to function mainly as a development regulating factor, a tissue-specific regulating factor, and a cell cycle regulating factor, there are also ones whose action is little clarified.

CITATION LIST

Non-Patent Literature

Non-Patent Literature 1: Eddy H van Roon, et al. Clinical Epigenetics 2013 Jan. 16; 5 (1):2. doi: 10.1186/1868-7083-5-2

SUMMARY OF INVENTION

Technical Problem

An object of the present invention is to provide a method which is capable of determining the differentiated state of the undifferentiated stem cells at an early stage of differentiation.

Solution to Problem

The present invention has been made in order to solve the problems, and consists of the following constitution.
(1) A method for determining a differentiated state of a cell comprising detecting an expression of FOXB2 gene of a stem cell, and determining the differentiated state based on the result.
(2) A differentiation marker selected from mRNA or a protein derived from FOXB2 gene.

It has been known that, when the undifferentiated cells such as ES cells or iPS cells are cultured in a medium supplemented with a basic FGF (bFGF, FGF2: basic fibroblast growth factor), the undifferentiated cells grow for a long period of time maintaining the undifferentiated state.

The present inventors have studied intensively to solve the problems, and as a result, have confirmed such phenomenon that, when iPS cells are cultured in a bFGF-free medium (differentiation-inducing treatment) in 3 to 5 days after initiation of culture, an expression of FOXB2 mRNA in iPS cells is detected, moreover an expression level thereof is significantly increased. In addition, it has also been confirmed that in iPS cells which are cultured in a medium supplemented with bFGF and are maintained in the undifferentiated state, an expression of FOXB2 mRNA is not confirmed. From the above, the present inventor have discovered that FOXB2 mRNA is useful as a differentiation marker of ES cells or iPS cells, and it is possible to select the cells at an early stage of differentiation by measuring an expression thereof, and have thus completed the present invention.

Advantageous Effects of Invention

The differentiated state of the stem cells can be determined at an early stage of differentiation by carrying out the method of the present invention. In addition, the present invention is applicable to the quality control of the stem cells, or to preparation and isolation methods for the differentiated cells. Further, since the present invention is capable of determining the differentiated cells at an early stage of the cell culture, the present invention is useful for an early stage screening of cells and for quality control of the stem cells. Further, reduction in culturing period, or cost reduction in expenditure regarding a culture medium, or the like, can be expected.

BRIEF DESCRIPTION OF DRAWINGS

FIG. 1 is an electrophoresis diagram obtained in Example 1, showing detection result of the expression of FOXB2 mRNA in hiPS cells, by an RT-PCR method. In FIG. 1, (1) shows detection result of the expression of FOXB2 mRNA; (2) shows detection result of the expression of GAPDH mRNA; (3) shows detection result of the expression of OCT3/4 mRNA; (4) shows detection result of the expression of NANOG mRNA; and (5) shows detection result of the expression of SOX2 mRNA.

FIG. 2 is an electrophoresis diagram obtained in Example 2, showing investigation result of the expression of FOXB2 mRNA by the RT-PCR method.

FIG. 3 is an electrophoresis diagram obtained in Example 3, showing investigation result of the expression of FOXB2 mRNA by the RT-PCR method.

FIG. 4 is an electrophoresis diagram obtained in Example 4, showing investigation result of the expression of Foxb2 mRNA by the RT-PCR method.

FIG. 5 is a photograph obtained in Reference Example 1, showing hiPS cells cultured in a bFGF-free medium (FIG. 5 (1)), and hiPS cells cultured in a medium containing bFGF (FIG. 5 (2)).

DESCRIPTION OF EMBODIMENTS

The stem cell involved in the present invention includes cells having so-called self-replicating potency and differentiation potency enabling differentiation into various cells. For example, undifferentiated cells having multiple differentiation potency (pluripotency) such as ES cells, iPS cells, ntES cells (nuclear transfer embryonic stem cells), EG cells (embryonic germ cells), EC cells (embryonic cancer stem cells), and the like are included.

In addition, animals from which a stem cell is derived include, for example, mammal such as human, cow, horse, dog, guinea pig, mouse, rat, and the like.

The stem cell which is a test cell to be subjected to the method for determining the differentiated state of a cell of the present invention includes a stem cell that have been subjected to known differentiation-inducing treatment, a stem cell that have been subjected to treatment for maintaining the undifferentiated state, a dedifferentiated somatic cell that has been subjected to known pluripotent-inducing treatment, and the like.

The method for differentiation-inducing treatment of an undifferentiated stem cell may be any method known per se, and is not especially limited. For example, there is included a method for culturing an undifferentiated stem cell in differentiation-inducing environment such as a method for culturing cells after treatment with a known differentiation-inducing agent or a method for culturing a cell in a medium not containing bFGF or LIF, or the like.

A chemical substance which induces differentiation of an undifferentiated stem cell (differentiation-inducing agent) includes retinoic acid which induces differentiation into nerve cells; spermine, sodium butyrate, and trichostatin A, which induces differentiation into cardiomyocytes; a DNA methyltransferase inhibitor which induces differentiation of mouse ES cells into insulin-producing cells, or the like.

"The undifferentiated state" means, for example, that cell is in a state of having self-replicating potency as described above and differentiation potency to differentiate into various cells.

"Treatment for maintaining the undifferentiated state" may be, for example, a known method for maintaining the undifferentiated state of a stem cell, and there is included, for example, co-culture with feeder cells, the addition of bFGF or LIF into a culture medium, or the like.

FOXB2 gene involved in the present invention means gene DNA, RNA, or the like, encoding FOXB2 protein which is present in the animal species from which cell to be subjected to determination is derived. In addition, gene encoding homolog, variant, and derivative of FOXB2 protein are also included in FOXB2 gene. Furthermore, there are also included nucleotide sequences which hybridize with these genes under stringent conditions, and genes containing the same, and genes having the nucleotide sequence which has a sequence homology of 70% or more, preferably 80% or more, more preferably 95% or more, and still more preferably 97% or more, to FOXB2 gene, and the like.

More specifically, for example, as the human FOXB2 gene, there is included gene corresponding to the nucleotide sequence shown in SEQ ID NO: 1 (nucleotide sequence of the human FOXB2 mRNA), gene having the nucleotide sequence encoding the protein shown in SEQ ID NO: 2, or gene having the nucleotide sequence which has a sequence homology of 70% or more, preferably 80% or more, more preferably 95% or more, and still more preferably 97% or more, to these nucleotide sequences.

For example, as a mouse Foxb2 gene, there is included gene corresponding to the nucleotide sequence shown in SEQ ID NO: 34 (nucleotide sequence of the mouse Foxb2 mRNA), gene having the nucleotide sequence encoding the protein shown in SEQ ID NO: 35, or gene having the nucleotide sequence which has a sequence homology of 70% or more, preferably 80% or more, more preferably 95% or more, and still more preferably 97% or more, to these nucleotide sequences.

FOXB2 mRNA involved in the present invention includes mRNA which is transcribed from FOXB2 gene, existing in the animals from which the cell to be subjected to determination is derived, for example, mRNA derived from FOXB2 gene.

The mRNA derived from FOXB2 gene, for example, the human FOXB2 mRNA includes the following ones:
  mRNA having the nucleotide sequence shown in SEQ ID NO: 1 (GenBank Accession No. NM_001013735),
  mRNA having the nucleotide sequence which has a sequence homology of 70% or more, preferably 80% or more, more preferably 95% or more, and still more preferably 97% or more, to the nucleotide sequences shown in SEQ ID NO: 1,
  mRNA encoding the amino acid sequence shown in SEQ ID NO: 2,
  mRNA encoding the amino acid sequence in which 1 or several amino acids, preferably 1 to 5 amino acids, and more preferably 1 to 3 amino acids in the amino acid sequence shown in SEQ ID NO: 2 are deleted, inserted, added, or substituted,
  mRNA encoding the amino acid sequence which has a sequence homology of 70% or more, preferably 80% or more, more preferably 95% or more, and still more preferably 97% or more, to the amino acid sequence shown in SEQ ID NO: 2.

For example, as the mouse Foxb2 mRNA, the following ones, and the like, are included:

mRNA having the nucleotide sequence shown in SEQ ID NO: 34 (GenBank Accession No. NM_008023), mRNA having the nucleotide sequence which has a sequence homology of 70% or more, preferably 80% or more, more preferably 95% or more, and still more preferably 97% or more, to the nucleotide sequences shown in SEQ ID NO: 34, mRNA encoding the amino acid sequence shown in SEQ ID NO: 35, mRNA encoding the amino acid sequence in which 1 or several amino acids, preferably 1 to 5 amino acids, and more preferably 1 to 3 amino acids in the amino acid sequence shown in SEQ ID NO: 35 are deleted, inserted, added, or substituted, mRNA encoding the amino acid sequence which has a sequence homology of 70% or more, preferably 80% or more, more preferably 95% or more, and still more preferably 97% or more, to the amino acid sequence shown in SEQ ID NO. 35.

FOXB2 protein involved in the present invention includes protein, which is translated from FOXB2 gene, existing in the animals from which the cells to be subjected to determination are derived. It may be a homolog, a variant, and a derivative of such FOXB2 protein.

For example, as the human FOXB2 protein, the following ones, and the like, are included:

The one that has the amino acid sequence shown in SEQ ID NO: 2, or the amino acid sequence in which 1 or several amino acids, preferably 1 to 5 amino acids, and more preferably 1 to 3 amino acids thereof are deleted, inserted, substituted, or added, The one that has the amino acid sequence which has a sequence homology of 70% or more, preferably 80% or more, more preferably 95% or more, and still more preferably 97% or more, to the amino acid sequences shown in SEQ ID NO: 2.

As the mouse FOXB2 protein, the following ones, and the like, are included:

The one that has the amino acid sequence shown in SEQ ID NO: 35, or the amino acid sequence in which 1 or several amino acids, preferably 1 to 5 amino acids, and more preferably 1 to 3 amino acids thereof are deleted, inserted, substituted, or added, The one that has the amino acid sequence which has a sequence homology of 70% or more, preferably 80% or more, more preferably 95% or more, and still more preferably 97% or more, to the amino acid sequences shown in SEQ ID NO: 35.

<I. Method for Determining Differentiated State of Cell of the Present Invention>

The method for determining the differentiated state of a cell of the present invention is "a method for determining a differentiated state of a cell comprising detecting an expression of FOXB2 gene in a stem cell, and determining the differentiated state based on the result".

<I-1. Method for Detecting Expression of FOXB2 Gene>

The method for detecting the expression of FOXB2 gene includes a method for detecting an expression of FOXB2 mRNA, or a method for detecting FOXB2 protein.

"Detecting expression" in the present invention encompasses the case of "detecting whether FOXB2 gene is expressed (for example, presence or absence of FOXB2 mRNA or FOXB2 protein)", and the case of "measuring an amount of the expression of FOXB2 gene (for example, an amount of FOXB2 mRNA or an amount of FOXB2 protein)."

Detection of the expression of FOXB2 gene is carried out after the test cell, which has been subjected to differentiation-inducing treatment, expressed FOXB2 mRNA or FOXB2 protein to a detectable extent. Specifically, after the test cell is subjected to differentiation-inducing treatment, the cell is cultured at an upper limit of within 7 days, preferably within 6 days, and more preferably within 5 days, and at a lower limit of more than one day, preferably 2 days or more, and more preferably 3 days or more. Then the cells are collected, and the following detection of the expression of FOXB2 gene may be carried out. During this time, the cells may be collected every day and detection of the expression of FOXB2 gene may be carried out.

(1) Method for Detecting Expression of FOXB2 mRNA

A method for detecting the expression of FOXB2 mRNA is not especially limited, as long as it is a method known per se for detecting mRNA, and may be selected as appropriate from known methods.

For example, there is included RT-PCR method (Reverse Transcription Polymerase Chain Reaction), real-time RT-PCR method, competitive PCR method, in situ PCR method, in situ hybridization method, DNA array method, Northern hybridization, FISH method, dot blot method, RNase protection assay method, RT-LAMP method, SmartFlare™ method using a complementary strand (capture strand) to the target RNA which is attached to gold nanoparticles and using a reporter strand that is a complementary strand of the capture strand, detection method using two kinds of fluorescent probes (Reduction-triggered fluorescence activation probe, RETF probe) having a sequence corresponding to the target RNA, a detection method utilizing an aromatic nucleophilic substitution reaction (method using a CNs-AMCA probe modified with amino coumarin which is protected by a 2-cyano-4-nitrobenzenesulfonyl group bound with DNA complementary to the target RNA, and an MBA probe modified with a thiophenol group bound with DNA complementary to the target RNA), or the like.

1) RT-PCR Method

RT-PCR method is a method in which, after synthesis of cDNA is carried out by the reverse transcription reaction using the target FOXB2 gene (for example, FOXB2 mRNA) as a template, DNA amplification is carried out by PCR [Kawasaki, E. S., et al., Amplification of RNA. in PCR Protocol; A Guide to methods and applications, Academic Press, Inc., San Diego, 21-27 (1991)]. Conditions of the reverse transcription reaction and the amplification reaction of DNA are not especially limited, and optimal conditions can be adopted as appropriate. In addition, an amplification region of the target gene (for example, FOXB2 mRNA) need not necessarily be the full length, and when there is no hindrance in confirmation of amplification products, the target may be a part of a region in the gene. An amount of the amplified cDNA (corresponding to the amount of mRNA) may be detected, for example, by using a probe that specifically hybridizes with an objective amplification fragment after subjecting a reaction solution of the DNA amplification to electrophoresis.

More specifically, for example, firstly mRNA is extracted and separated from the test cells by a known method. Then, RT-PCR method is carried out using a nucleotide chain having the nucleotide sequence corresponding to the nucleotide sequence of FOXB2 mRNA as a primer for amplification, and using mRNA obtained above as a template, thereby, single-stranded DNA (cDNA) complementary to FOXB2 mRNA or a part of the region thereof is synthesized and amplified. Then, it is possible to detect the presence or the amount of FOXB2 mRNA in the cells by detection of presence or absence, or quantity (amount) of the amplification products (cDNA).

An amplification primer to be used in the above, for example, the amplification primer in the case of detecting the human FOXB2 mRNA includes, for example, a primer having the nucleotide sequence shown in SEQ ID NO: 4. The amplification primer in the case of detecting the mouse Foxb2 mRNA includes, for example, a primer having the nucleotide sequence shown in SEQ ID NO: 37.

Furthermore, when the presence or absence, or more or less (amount) of amplification products is detected by further carrying out nucleic acid amplification reaction such as a PCR method according to a usual method using cDNA amplified in the method described above as a template, and using a primer pair prepared based on the nucleotide sequence of FOXB2 mRNA so as to be able to amplify a target region of FOXB2 mRNA, the presence or amount of FOXB2 mRNA can be detected more accurately. Detection of the amplification products may be carried out by a usual electrophoresis method for detecting the amplification products, or the like.

When the nucleic acid amplification reaction is carried out using cDNA amplified by the above method as a template, it may be carried out by a real-time amplification detection method. The detection method by the real-time amplification detection method includes, for example, a real-time PCR detection method.

As an example of the real-time PCR detection method, there is included a usual intercalator method for carrying out a real-time PCR using an intercalator (for example, SYBR™ Green I), TaqMan™ real-time PCR method, MGB Eclipse Probe System method, Molecular Beacons Probe Technology method, LUX Fluorogenic Primer method, Quenching probe-PCR (QP) method, cycle Riningu probe method, or the like, but is not limited thereto.

"The primer pair prepared so as to be able to amplify the target region of FOXB2 mRNA" used in the PCR (including real-time PCR), includes a primer pair which amplifies the nucleotide sequence of FOXB2 mRNA, or a specific region thereof (partial sequence).

Such primer pair includes, for example, a primer pair for amplification of the human FOXB2 mRNA (the nucleotide sequence shown in SEQ ID NO: 1) or a specific region thereof (partial sequence). Specifically, for example, when the 179 bp of the 45th to 223rd region (SEQ ID NO: 3) in the nucleotide sequence shown in SEQ ID NO: 1 is targeted, there is included a primer pair of a primer having the nucleotide sequence shown in SEQ ID NO: 9 and a primer having the nucleotide sequence shown in SEQ ID NO: 10.

In addition, it may also include, for example, a primer pair for amplification of the mouse Foxb2 mRNA (the nucleotide sequence shown in SEQ ID NO: 34), or a specific region thereof (partial sequence). Specifically, for example, when the 169 bp of the 132nd to 300th region (SEQ ID NO: 36) in the nucleotide sequence shown in SEQ ID NO: 34 is targeted, there is included a primer pair of a primer having the nucleotide sequence shown in SEQ ID NO: 45, and a primer having the nucleotide sequence shown in SEQ ID NO: 46.

The primer for amplification of the FOXB2 mRNA is commercially available in various types, so they may be used.

Taking a detection method for the human FOXB2 mRNA by the RT-PCR method as an example, it is described specifically as follows.

To 500 ng to 10 μg of total RNA which is extracted from the test cells and subjected to DNase treatment, 1 μL of a 1 to 10 μM amplification primer of FOXB2 mRNA (for example, the primer having the nucleotide sequence shown in SEQ ID NO: 4) is added, and incubated at 65 to 80° C. for 2 to 5 minutes, then, under ice-cooling, 4 μL of a 5× Buffer, 4 μL of 2.5 mM dNTPs, 0.5 μL (20 U) of an RNase Inhibitor, and 1 μL (100 U) of reverse transcriptase (ReverTra Ace) are added thereto, and total volume is made to 20 μL with distilled water and mixed, then warmed at 37 to 50° C. for 20 to 60 minutes, thereby a reverse transcription reaction is carried out. Then, the resulting cDNA is recovered by a usual method.

After that, 1 μL of the resulting cDNA, 5 μL of distilled water, 12.5 μL of a 2×PCR Buffer, 4 μL of 2 mM dNTPs, 0.5 μL (0.5 U) of DNA polymerase (KOD FX Neo), 1 μL of a 5 to 10 μM forward primer (for example, the primer having the nucleotide sequence shown in SEQ ID NO: 9), and 1 μL of a 5 to 10 μM reverse primer (for example, the primer having the nucleotide sequence shown in SEQ ID NO: 10) are mixed. Then, for example, a reaction at 94° C. for 2 minutes, at 98° C. for 10 seconds→at 56° C. for 20 seconds→at 68° C. for 30 seconds is carried out for about 28 to 30 cycles.

After the PCR is finished, the detection and the analysis of amplification products is carried out, for example, by electrophoresis to detect FOXB2 mRNA.

Alternatively, after recovering cDNA, the real-time PCR is carried out using an intercalator (for example, SYBR™ Green I), and, for example, the same forward primer and reverse primer as above, cDNA obtained above as a template, and a polymerase such as Taq DNA polymerase. And, by measuring fluorescence intensity of the intercalator that intercalates in correlation with the amount of the amplification products, the detection and the analysis of the amplification products are carried out, and thus detection of FOXB2 mRNA is carried out.

Furthermore, after carrying out the nucleic acid amplification reaction using cDNA amplified by the above method as a template, the detection and the analysis of the amplification products may be carried out by a capillary electrophoresis method (J. Chromatogr. 593 253-258 (1992); Anal. Chem. 64 1926-1932 (1992); WO2007/027495, or the like), or by capillary chip electrophoresis. That is, after recovering cDNA, for example, through use of a labeled primer with a labeling substance such as fluorescent material, or a intercalator, or the like, a signal derived from the labeled PCR amplification products separated by capillary chip electrophoresis may be detected by a detector. As the detector, equipment such as a differential refractive detector, a fluorescence detector, and a UV detector may be adopted, and among them the UV detector and the fluorescence detector are preferable, and the fluorescence detector is more preferable. For example, using the automatic immunoassay analyzer such as LiBASys (manufactured by Shimadzu Co., Ltd.), operation from the PCR to electrophoresis can be carried out in real time.

2) Northern Hybridization Method

A method for detecting FOXB2 mRNA by a Northern hybridization method includes, for example, a method in which mRNA extracted and separated from the test cells is immobilized on an appropriate carrier, and subjected to hybridization with a labeled probe (may be cDNA) having a nucleotide sequence complementary to FOXB2 mRNA, and FOXB2 mRNA in the test cells is detected by detecting a degree of hybridization. The probe to be used herein may be the one consisted of the entire sequence complementary to the nucleotide sequence of FOXB2 mRNA, or the one consisted of a part of the nucleotide sequence thereof. In addition, for this detection method, a microarray to which the probe is immobilized or a DNA chip to which the probe is immobilized may be used.

It should be noted that, as to a reagent to be used in the method for detecting FOXB2 mRNA involved in the present invention, any reagent usually used in this field which neither inhibit the stability of the coexisting reagents nor inhibit the nucleic acid amplification reaction such as PCR and hybridization reaction, for example, buffering agent, stabilizer, preservative, and the like can be used. In addition, concentrations of the reagents may be selected as appropriate from a range of concentration usually used in this field.

Specific example of buffer solution includes all kinds of buffer solutions usually used for performing PCR and hybridization reaction, for example, Tris buffer, phosphate buffer, Veronal buffer, borate buffer, Good's buffer and the like; and the pH of the buffer solution is not particularly limited, but generally a range between pH 5-9 is included.

In addition, if needed, nucleic acid synthetase (DNA polymerase, RNA polymerase, reverse transcriptase and the like), enzyme-specific substrate (dNTP, rNTP and the like), double strand intercalator (ethidium bromide, SYBR™ Green and the like), signal detection substance such as FAM, TAMRA or the like, may be used.

It should be noted that, when the in situ PCR method or the in situ hybridization method is carried out, detection of FOXB2 mRNA may be carried out without destroying the test cells.

(2) Method for Detecting Expression of FOXB2 Protein

1) Method for Detecting the Expression without Destroying a Cell

Since FOXB2 protein is a transcription factor, it exists in a nucleus of a cell.

Since a technique for staining a nuclear material without destroying cells has been developed, it is possible to detect the intranuclear FOXB2 protein without destroying cells by using the technique. For example, a nuclear membrane of the test cells is partially solubilized using a buffer solution containing a surfactant, such as Triton, NP-40, Tween20™ Saponin, Digitonin™, Leucoperm™. It follows that a gap which antibodies can pass through is generated in the cell membrane without destroying the structure. FOXB2 protein in the nucleus can be detected by carrying out staining of the nuclear protein using an anti FOXB2 antibody labeled with a fluorescent substance or the like.

In addition, various reagents to stain the intranuclear material are also commercially available. Thus, the expression of FOXB2 protein may be detected by staining FOXB2 protein in the nucleus using these commercially available reagents.

2) Method for Detecting a Cell after Destroying them

In addition, FOXB2 protein can also be detected by carrying out the following method for destroying a cell.

Firstly, the cells or fungus bodies are collected by subjecting culture of the test cells to a usual method, such as filtration or centrifugal separation, and suspended in an appropriate buffer solution. After destroying cell wall and/or cell membrane of the cells, or the like, by a method such as surfactant treatment, ultrasonic treatment, lysozyme treatment, freezing and thawing, or the like, extract containing FOXB2 protein is obtained by a method such as centrifugation or filtration.

Then, the resulting FOXB2 protein in the extract may be detected by a method known per se for detecting protein.

The method for detecting FOXB2 protein in the extract includes a method in accordance with immunoassay known per se, for example, a method for using a substance having affinity to FOXB2 protein (for example, an antibody, or the like), that is, so-called enzyme immunoassay (EIA), radioimmunoassay (MA), enzyme-linked immunosorbent assay (ELISA), fluorescence immunoassay (FIA), a western blotting method, an immunohistochemical method, an antibody array method, an assay method according to a simple immunochromatography, or the like; methods by combination of these methods with high performance liquid chromatography (HPLC), an electrophoresis method, a capillary electrophoresis method, a capillary chip electrophoresis method, or the like. Measurement principle thereof includes, for example, a sandwich method, a competitive method, a double antibody method, or the like, but is not limited thereto. Specific conditions of these measurement methods can be set as appropriate by those skilled in the art.

In addition, FOXB2 protein may be detected by a measurement method according to a immunoagglutination method, such as nephelometric immunoassay, turbidimetric immunoassay, etc. These detection methods may also be carried out according to a method known per se.

In the method for 1) and 2), an antibody against FOXB2 protein to be used to detect FOXB2 protein (the anti-FOXB2 antibody) may be any antibody which is capable of recognizing FOXB2 protein or its partial peptide, or salts thereof, and is not especially limited.

For example, it may be any of polyclonal antibodies or monoclonal antibodies, and it is optional to use these alone or in combination as appropriate. In addition, if needed, $F(ab')_2$, Fab' or Fab, which is prepared by digesting them using an enzyme, such as pepsin, papain, or the like, may be used. Further, it is also possible to use commercially available antibodies against FOXB2 protein.

The antibody may be labeled with a labelling substance. The labelling substance to be used for labeling includes enzymes to be used in EIA (ELISA), for example, alkali phosphatase, β-galactosidase, peroxidase, micro-peroxidase, glucose oxidase, glucose-6-phosphate dehydrogenase, acetylcholine esterase, malate dehydrogenase, luciferase, and the like; a radioactive isotope to be used in RIA, for example, $^{99m}Tc$, $^{131}I$, $^{125}I$, $^{14}C$, $^{3}H$, or the like; a fluorescent substance to be used in FIA, for example, fluorescein, dansyl, fluorescamine, coumarin, naphthylamine, or a derivative thereof, or the like; a luminescent substance, for example, luciferin, isoluminol, luminol, bis(2,4,6-trifluorophenyl) oxalate, or the like; a substance having absorption in an ultraviolet region, for example, phenol, naphthol, anthracene, or the like; a substance having properties as a spin labeling agent represented by a compound having an oxyl group, for example, 4-amino-2,2,6,6-tetramethylpiperidine-1-oxyl, 3-amino-2,2,5,5-tetramethylpyrrolidine-1-oxyl, 2,6-di-t-butyl-α-(3,5-di-t-butyl-4-oxo-2,5-cyclohexadiene-1-ylidene)-p-tolyl oxyl, or the like.

Specific examples of the antibody against FOXB2 protein include, for example, "an antibody against a protein having the amino acid sequence shown in SEQ ID NO: 2" or "an antibody against a protein having the amino acid sequence shown in SEQ ID NO: 35".

In addition, reagents and concentrations in detection thereof, measurement conditions for carrying out the detection (reaction temperature, reaction time, pH in the reaction, measurement wavelength, measuring equipment, or the like) to be used to detect FOXB2 protein described above may be set all according to a measurement procedure of the immunological assay method known per se, as described above. As for an automatic analyzer, spectrophotometer, or the like, anyone which have usually used in this field, can be used without exception.

<I-2. Method for Determining Differentiated State of Cell>

Based on the results obtained by detecting the expression of FOXB2 gene in the stem cells by the method described above, the differentiated state of the test cell is determined.

"Differentiated/have been differentiated" or "the differentiated state" in the present invention encompasses the case where the cell is in either of a state of "an early stage of differentiation", a state "which has acquired differentiation potential to differentiate in the future (differentiation induced state)", and "the differentiated" state.

Preferably, "differentiated/have been differentiated" or "the differentiated state" in the present invention is a case in either of a state of a cell in "an early stage of differentiation" or a state of a cell "which has acquired differentiation potential to differentiate in the future (differentiation induced state)".

An "early stage of differentiation" in the present invention refers to a short period of time after differentiation-inducing treatment, specifically, a period of up to 7 days, preferably up to 6 days, and more preferably up to 3 to 5 days, after differentiation-inducing treatment.

Alternatively, an "early stage of differentiation" in the present invention encompasses a stage before the undifferentiated stem cell differentiate into any of the three germ layers, or a stage before disappearance of undifferentiation markers (for example, OCT3/4, NANOG, SOX2, or the like) after differentiation-inducing treatment.

The method for determining the differentiated state of the present invention includes, for example, the following methods.

(1) Method for Determining Based on Detection Results of Expression of FOXB2 mRNA The method for determining based on detection result of FOXB2 mRNA includes, for example, the following methods.

1) Detection of FOXB2 mRNA in the test cells is carried out according to the method described above, and it is determined that the test cells are in the differentiated state when FOXB2 mRNA is detected.

2) Detection of FOXB2 mRNA in the test cells is carried out, and as a comparison, the detection of FOXB2 mRNA is carried out in the same manner using undifferentiated stem cells that have been confirmed to be in the undifferentiated state. In this case, when the amount of FOXB2 mRNA in the test cells is greater than the detected amount of FOXB2 mRNA in undifferentiated stem cells to be compared, it is determined that the test cells are in the differentiated state. At this time, the determination of whether the detected amount of FOXB2 mRNA in the test cells is greater than the detected amount of FOXB2 mRNA in the undifferentiated stem cells to be compared may be relatively determined by comparing the both amount.

3) Examination of whether the detected amount of FOXB2 mRNA in the test cells is greater than the detected amount of FOXB2 mRNA in the undifferentiated stem cells to be compared may be carried out by comparing detected amount of FOXB2 mRNA in the test cells with the detected amount of FOXB2 mRNA in the undifferentiated stem cells which was measured in advance. When the detected amount of FOXB2 mRNA in the test cells is greater than the detected amount of FOXB2 mRNA in the undifferentiated stem cells which was measured in advance, it is determined that the test cells are in the differentiated state.

4) A boundary value (cut-off value) that is capable of determining whether or not the test cells are in the differentiated state is set in advance. The differentiated state of the test cells may be determined from whether the detected amount of FOXB2 mRNA in the test cells is higher than the boundary value. In this case, when the detected amount of FOXB2 mRNA in the test cells is higher than the cut-off value, it is determined that the test cells are in the differentiated state.

(2) Method for Determination Based on Detection Results of FOXB2 Protein

The method for determination based on the detection results of FOXB2 protein, includes, for example, the following methods.

1) Detection of FOXB2 protein in the test cells is carried out according to the method described above, and it is determined that the test cells are in the differentiated state when FOXB2 protein is detected.

2) The detection of FOXB2 protein in the test cells is carried out, and as a comparison, the detection of FOXB2 protein is carried out in the same manner using the undifferentiated stem cells that have been confirmed to be in the undifferentiated state. In this case, when the detected amount of FOXB2 protein in the test cells is greater than the detected amount of FOXB2 protein in the undifferentiated stem cells to be compared, it is determined that the test cells are in the differentiated state. At this time, the determination of whether the detected amount of FOXB2 protein in the test cells is greater than the detected amount of FOXB2 protein in the undifferentiated stem cells to be compared may be relatively determined by comparing the both amount.

3) Examination of whether the detected amount of FOXB2 protein in the test cells is greater than the detected amount of FOXB2 protein in undifferentiated stem cells to be compared may be carried out by comparing detected amount of FOXB2 protein in the test cells with the detected amount of FOXB2 protein in the undifferentiated stem cells which was measured in advance. When the detected amount of FOXB2 protein in the test cells is greater than the detected amount of FOXB2 protein in the undifferentiated stem cells which was measured in advance, it is determined that the test cells are in the differentiated state.

4) A boundary value (cut-off value) that is capable of determining whether or not the test cells are in the differentiated state is set in advance. The differentiated state of the test cells may be determined from whether detected amount of FOXB2 protein in the test cells is higher than the boundary value. In this case, when the detected amount of FOXB2 protein in the test cells is higher than the cut-off value, it is determined that the test cells are in the differentiated state.

A method for determining the differentiated state of a cell of the present invention may be carried out, specifically, for example, by the following method.

The undifferentiated stem cells (test cells) such as iPS cells or ES cells are subjected to differentiation-inducing treatment by a known method. Subsequently, after the differentiation-inducing treatment, the cells are cultured for at an upper limit of within 7 days, preferably within 6 days, and more preferably within 5 days, and at a lower limit of more than one day, preferably 2 days or more, and more preferably 3 days or more, the cells are collected, and the expression of FOXB2 gene (the expression of FOXB2 mRNA, or the expression of FOXB2 protein) is detected by the above method. Then, when the expression of FOXB2 gene is confirmed, it is determined that the cells are in the differentiated state (including the case where "the cells in the differentiated state is present in the cell population"; hereinafter, the same as above).

Alternatively, the detection of the expression of FOXB2 gene (detection of FOXB2 mRNA or FOXB2 protein) in the test cells is carried out, and as a comparison, the detection of the expression of FOXB2 gene is carried out in the same manner using the undifferentiated stem cells that have been confirmed to be in the undifferentiated state. In this case, when the detected amount of the expression of FOXB2 gene (the expression level of FOXB2 mRNA, or the expression level of FOXB2 protein) in the test cells is greater than an detected amount of the expression of FOXB2 gene in the undifferentiated stem cells to be compared, it is determined that the test cells are in the differentiated state.

In addition, the detected amount of the expression of FOXB2 gene (the detected amount of FOXB2 mRNA or of FOXB2 protein) in the undifferentiated stem cells, which was measured in advance, is compared with the detected amount of the expression of FOXB2 gene in the test cells. In this case, when the detected amount of the expression of FOXB2 gene in the test cells is greater than the detected amount of the expression of FOXB2 gene in the undifferentiated stem cells to be compared, it is determined that the test cells are in the differentiated state.

Further, the boundary value (cut-off value) that is capable of determining whether or not the test cells are in the differentiated state is set in advance. In this case, when the detected amount of the FOXB2 mRNA or the detected amount of the FOXB2 protein in the test cells is higher than the boundary value, it is determined that the test cells are in the differentiated state.

Furthermore, as for undifferentiated stem cells which have not been subjected to differentiation-inducing treatment, when the method for determining the differentiated state of the present invention is carried out, it is also possible to confirm whether the undifferentiated stem cells have maintained the undifferentiated state.

(3) Application of the Present Invention

The method for determining the differentiated state of a cell of the present invention can be applied further to the following methods.

1) Application to a Method for Screening of Cells

For a sample containing a certain group of cells, FOXB2 mRNA of the cells constituting the certain group is detected by the method of the present invention. Then, when FOXB2 mRNA is detected, it is determined that cells in the differentiated state are present in the sample (meaning of the "differentiated state" is the same as described above. Hereinafter, the same as above.); and when FOXB2 mRNA is not detected, it may be determined that cells in the differentiated state are not present in the sample. Alternatively, the expression of FOXB2 protein in the sample is detected. In this case, when FOXB2 protein is detected, it is determined that cells in the differentiated state is present in the sample; and when FOXB2 protein is not detected, it may be determined that cells in the differentiated state are not present in the sample.

2) Application to Quality Control of Stem Cells

By detecting the expression of FOXB2 gene (detection of FOXB2 mRNA or FOXB2 protein) in stem cells which have been subjected to known differentiation-inducing treatment according to the method of the present invention, it can be determined whether the cells are in the differentiated state, or in a state where undifferentiated stem cells are mixed therein. Therefore, the method of the present invention can be applied to quality control of the differentiated cells.

In addition, by detecting the expression of FOXB2 gene (detection of FOXB2 mRNA or the FOXB2 protein) according to the method of the present invention in stem cells which have been subjected to treatment for maintaining the undifferentiated state, it can be confirmed whether the cells are maintaining the undifferentiated state. Therefore, the method of the present invention can be applied to quality control of undifferentiated stem cells.

3) Application to a Method for Quality Inspection of a Culture Medium

In order to culture undifferentiated stem cells while maintaining the undifferentiated state thereof, the medium is required to be, for example, a medium which does not contain differentiation-inducing factors, and which is capable of culturing the undifferentiated stem cells while maintaining the undifferentiated state. By using the method for determining the differentiated state of the present invention, it is possible to carry out quality inspection of such a medium.

For example, after culturing undifferentiated stem cells in a medium to be determined for several days, for example, for approximately 3 to 7 days, and usually for approximately 5 to 6 days, detection of the expression of FOXB2 mRNA in the cells is carried out; and when the expression of FOXB2 mRNA is not detected, it can be determined that the medium is capable of culturing stem cells while maintaining the undifferentiated state of the stem cells. Alternatively, in the detection of the expression of FOXB2 protein in cells after cultivation, when the expression of FOXB2 protein is not detected, it can be determined that the medium is the one capable of culturing while maintaining the undifferentiated state of stem cells.

4) Application to a Method for Preparation and Isolation of Differentiated Cells The differentiated cells can be prepared and isolated by applying the method of the present invention.

For example, according to "1) A method for detecting expression without destroying cells" described in "(2) Method for Detecting Expression of FOXB2 Protein", an anti FOXB2 protein antibody labeled with a labeling substance is reacted with cells which contain or suspected to contain cells in the differentiated state. The cells in the differentiated state can be prepared and isolated by separating and purifying only fluorescent labeled cells by a method such as flow cytometry.

Undifferentiated stem cells can be prepared and isolated by separating and purifying only cells not fluorescently labeled by a method such as flow cytometry in the same manner as described above.

5) Application to a Method for Screening of Differentiation-Inducing Factors

The present invention can be applied to a method for confirming whether a certain substance has ability to induce differentiation of undifferentiated stem cells.

For example, after culturing undifferentiated stem cells in a medium containing a test substance for several days, for example, for 3 to 7 days, and usually for approximately 5 to 6 days, the expression of FOXB2 mRNA in the cultured cells is detected; and when FOXB2 mRNA is detected, the test substance is confirmed to induce differentiation of the undifferentiated stem cells. Alternatively, in detection of the expression of FOXB2 protein in the cultured cells, when the expression of FOXB2 protein is detected, the test substance is confirmed to induce differentiation of undifferentiated stem cells.

<II. Differentiation Marker of the Present Invention>

The differentiation marker of the present invention includes "a differentiation marker selected from mRNA or protein derived from FOXB2 gene". Specifically, the differentiation marker of the present invention is a differentiation marker of a stem cell. Specific examples of the stem cell is as described above.

"mRNA or protein derived from FOXB2 gene" includes FOXB2 mRNA and FOXB2 protein involved in the present invention. Specific examples thereof are as described above.

More specifically, for example, differentiation markers selected from the following (i)~(vii) are included.
(i) mRNA having the nucleotide sequence shown in SEQ ID NO: 1 or SEQ ID NO: 34,
(ii) mRNA having a nucleotide sequence which has a sequence homology of 70% or more, preferably 80% or more, more preferably 95% or more, and still more preferably 97% or more, to the nucleotide sequence shown in SEQ ID NO: 1 or SEQ ID NO: 34,
(iii) mRNA encoding an amino acid sequence shown in SEQ ID NO: 2 or SEQ ID NO: 35,
(iv) mRNA encoding an amino acid sequence in which 1 or several amino acids, preferably 1 to 5 amino acids, and more preferably 1 to 3 amino acids in the amino acid sequence shown in SEQ ID NO: 2 or SEQ ID NO: 35 are deleted, inserted, substituted, or added,
(v) mRNA encoding an amino acid sequence which has a sequence homology of 70% or more, preferably 80% or more, more preferably 95% or more, and still more preferably 97% or more, to the amino acid sequence shown in SEQ ID NO: 2 or SEQ ID NO: 35,
(vi) a protein having the amino acid sequence shown in SEQ ID NO: 2 or SEQ ID NO: 35, or an amino acid sequence in which 1 or several amino acids, preferably 1 to 5 amino acids, and more preferably 1 to 3 amino acids thereof are deleted, inserted, substituted, or added,
(vii) a protein having an amino acid sequence which has a sequence homology of 70% or more, preferably 80% or more, more preferably 95% or more, and still more preferably 97% or more, to the amino acid sequence shown in SEQ ID NO: 2 or SEQ ID NO: 35.

<III. Kit for Determining Differentiated State Involved in the Present Invention>

A kit for determining the differentiated state of a cell involved in the present invention includes a kit provided with reagents for detecting the expression of FOXB2 gene, or a kit provided with reagents for measuring an expression level of FOXB2 gene.

For example, the followings are included.
(a) A kit provided with a primer or a labeled substance thereof for use in detecting expression of FOXB2 mRNA or in measuring the expression level thereof,
(b) A kit provided with an antibody against FOXB2 protein (an antibody that recognizes FOXB2 protein, preferably an antibody that specifically binds to FOXB2 protein) or a labeling substance of the antibody for use in detecting the expression of FOXB2 protein, or in measuring the expression level thereof.

Preferable aspects and specific examples of a component of the reagents constituting the kit are as described above.

An example of "the primer for use in detecting the expression of FOXB2, or in measuring the expression level thereof" described above (a) includes, for example, "a primer to be used to detect the nucleotide sequence shown in SEQ ID NO: 1 or SEQ ID NO: 34, or a partial sequence thereof".

More specifically, it includes, for example,
(a-1) A primer pair used in the case of carrying out PCR using cDNA obtained by the reverse transcription reaction as a template, or
(a-2) A combination of an amplification primer used in the reverse transcription reaction, and a primer pair used in the case of carrying out PCR using cDNA obtained by the reverse transcription reaction as a template.

For the primers which constitute the primer pair of (a-1), at least one of which may be labeled with a labeling substance, as needed.

Specific examples of the primer pair of (a-1) include, "a primer pair of a primer having the nucleotide sequence shown in SEQ ID NO: 9, and a primer having the nucleotide sequence shown in SEQ ID NO: 10", or "a primer pair of a primer having the nucleotide sequence shown in SEQ ID NO: 45, and a primer having the nucleotide sequence shown in SEQ ID NO: 46".

Specific examples of (a-2) include "a combination of a primer shown in SEQ ID NO: 4, and a primer pair of a primer having the nucleotide sequence shown in SEQ ID NO: 9 and a primer having the nucleotide sequence shown in SEQ ID NO: 10", or "a combination of a primer shown in SEQ ID NO: 37, and a primer pair of a primer having the nucleotide sequence shown in SEQ ID NO: 45 and a primer having the nucleotide sequence shown in SEQ ID NO: 46".

Specific examples of "the antibody against FOXB2 protein for use in detecting the expression of FOXB2 protein, or in measuring the expression level thereof" of the above (b) are as described above.

For example, "an antibody against protein having the amino acid sequence shown in SEQ ID NO: 2 or SEQ ID NO: 35" is included.

The kit comprising the above (a-1) or (a-2) as a constituent may further contain reverse transcriptase to be used for a RT-PCR method, further as needed, the nucleic acid synthesizing enzyme (DNA polymerase, RNA polymerase, or the like), substrates corresponding to the enzyme (dNTPs, rNTPs, or the like), a double strand intercalator (SYBR™ Green, ethidium bromide, or the like), a label detection substance, such as FAM and TAMRA.

In addition, the kit comprising the above (a-1) or (a-2) as a constituent may contain, for example, a buffering agent, a stabilizing agent, a preservative, or the like, which does not inhibit stability of coexisting reagents, or the like, and does not inhibit a PCR, or a hybridization reaction. In addition, concentration thereof may also be selected as appropriate from a range of concentration usually used in this field.

Specific examples of a buffer solution include all of buffer solutions usually used in the case of carrying out a common PCR or a hybridization reaction, for example, Tris buffer solution, phosphate buffer solution, veronal buffer solution, borate buffer solution, Good's buffer solution, and the like. pH thereof is also not especially limited, and includes, for example, a range of 5 to 9.

Reagents contained in the kit having the above (b) as a constituent may have those normally used in this field, for example, buffering agent, sensitizing agent, surfactant, preservative (for example, sodium azide, salicylic acid, benzoic acid, or the like), stabilizing agent (for example, albumin, globulin, water-soluble gelatin, surfactant, saccharide, or the like), activating agent, effect avoidance agent of coexisting substances, and other ones used in this field, which do not inhibit stability of coexisting reagents, or do not inhibit an antigen-antibody reaction. In addition, concentration ranges of these reagents and the like may be used by selecting as appropriate from concentration ranges normally used in the measuring method known per se. Specific examples of the buffering agent, and the like, pH and concentration thereof are as described above.

In addition, (a-1), (a-2), (b) or the like which is contained in the kit for determining the differentiated state of cells involved in the present invention may be the one in a solution state such as suspension suspended in an appropriate buffer solution, or a frozen product or a freeze-dried product thereof. Specific examples of the buffering agent and the like used for this purpose, pH and concentration thereof are as described above.

Furthermore, a manual for use in the method for detecting the expression of the FOXB2 gene in a stem cell involved in the present invention (for example, the expression of the FOXB2 mRNA or the expression of the FOXB2 protein), or a manual for carrying out the method for determining the differentiated state of a cell of the present invention may be contained in the kit of the present invention. The "manual" means an instruction manual, a package insert, or a brochure (leaflet), or the like of the kit, in which features, principles, operational procedures, determination procedures, etc. of the method is described substantially by a text or by figures and tables, or the like.

Hereinafter, the present invention is explained more specifically based on Examples, however, scope of the present invention should not be limited thereto.

EXAMPLES

Example 1

Expression of FOXB2 mRNA and known undifferentiation markers of hiPS cells, which have been subjected to differentiation-inducing treatment, was detected by the RT-PCR method.

(1) Culture and Differentiation-Inducing Treatment of the Stem Cells hiPS cells (201B7 strain, Center for iPS Cell Research and Application, Kyoto University (iPS Academia Japan, Inc.)), and as a comparison, HDF cells that are the differentiated cells (normal human cell-derived fibroblast, produced by Lonza Japan Co., Ltd.) were subcultured for three times in a medium containing or not containing bFGF (100 ng/mL) (StemSure hPSC medium, produced by Wako Pure Chemical Industries, Ltd.), and cells were recovered on day 5 of culture.

(2) Extraction of Total RNA

Total RNA was extracted from the cells recovered in the above (1) using a kit ISOGEN (manufactured by Nippon Gene Co., Ltd.) which is a commercially available nucleic acid extraction reagent and according to the product instruction.

(3) DNase Treatment

To 1 µg of total RNA extracted in the above (2), distilled water was added to make a total volume of 17 µL, then 2 µL of a 10×Reaction Buffer (produced by Promega Corporation) and 1 µL (1 U) of RQ1 RNase-Free DNase (produced by Promega Corporation) were added and mixed, and incubated at 37° C. for 20 minutes. After that, 1 µL of a Stop Buffer (20 mM EGTA) (produced by Promega Corporation) was added and mixed, then incubated at 65° C. for, 10 minutes. Thereafter, 100 µL of a Binding Buffer (5.5 M guanidine hydrochloride, (produced by Wako Pure Chemical Industries, Ltd.), 20 mM Tris-HCl, pH 6.6) was added to the reactant and mixed, then transferred to an Econospin (a silica membrane spin column, for nucleic acid purification, manufactured by GeneDesign, Inc.), and centrifuged at 12000×G at room temperature for 1 minute to remove the solution in the tube. Subsequently, 500 µL of a Washing Buffer (2 mM Tris-HCl, pH 7.5 (produced by Nippon Gene Co., Ltd.), 80% ethanol (produced by Wako Pure Chemical Industries, Ltd.)) was added to the Econospin, and centrifuged at 12000×G at room temperature for 1 minute to remove the solution in the tube. Then, after additional centrifugal separation at 12000×G at room temperature for 1 minute, the tube was changed to a new tube, and 50 µL of an Elution Buffer (10 mM Tris-HCl, pH 8.0) (produced by Nippon Gene Co., Ltd.) was added, then centrifuged at 12000×G, at room temperature for 1 minute to recover total RNA. Thereafter, ethanol precipitation was carried out, and the resulting precipitate was dissolved in 9.5 µL of distilled water.

(4) Reverse Transcription Reaction

To 9.5 µL of total RNA which has been subjected to DNase treatment in the above (3), 1 µL of mixed Primer (each 5 µM) containing amplification primers targeting the following each mRNA was added. The following primers are all produced by Sigma-Aldrich Corporation.

primer for amplification of FOXB2 mRNA, CAGAAGCTACCCTTGCCAG (SEQ ID NO: 4, GenBank Accession No. NM_001013735: 242-260 (corresponding to the nucleotide sequence of a strand complementary to the nucleotide sequence of 242nd to 260th of the nucleotide sequence of GenBank Accession No. NM_001013735. Hereinafter the same as above.)

primer for amplification of OCT3/4 mRNA, GTTCTTGAAGCTAAGCTGCAG (SEQ ID NO: 5, GenBank Accession No. NM_002701: 641-661)

primer for amplification of NANOG mRNA, GTTCTGGAACCAGGTCTTCAC (SEQ ID NO: 6, GenBank Accession No. NM_024865: 631-651)

primer for amplification of SOX2 mRNA, GACCACACCATGAAGGCATTC (SEQ ID NO: 7, GenBank Accession No. NM_003106: 572-592)

primer for amplification of GAPDH mRNA, GTCTACATGGCAACTGTGAGG (SEQ ID NO: 8, GenBank Accession No. NM_002046: 1303-1323).

(GAPDH: glyceraldehyde-3-phosphate dehydrogenase).

Each mixture was incubated at 72° C. for 3 minutes, then immediately cooled with ice. Then, 4 µL of a 5× Buffer (produced by Toyobo Co., Ltd.), 4 µL of 2.5 mM dNTPs (produced by Nippon Gene Co., Ltd.), 0.5 µL (20 U) of an RNase Inhibitor, super (produced by Wako Pure Chemical Industries, Ltd.), and 1 µL (100 U) of ReverTra Ace (produced by Toyobo Co., Ltd.) were added thereto and mixed, and incubated at 42° C. for 50 minutes. Thereafter, 100 µL of a Binding Buffer (5.5 M guanidine hydrochloride (produced by Wako Pure Chemical Industries, Ltd.), 20 mM Tris-HCl, pH 6.6 (produced by Wako Pure Chemical Industries, Ltd.)) was added and mixed, then transferred to an Econospin (a silica membrane spin column for nucleic acid purification, manufactured by GeneDesign, Inc.) and centrifuged at 12000×G at room temperature for 1 minute to remove the solution in the tube. Subsequently, 500 µL of a Washing Buffer (2 mM Tris-HCl, pH 7.5 (produced by Nippon Gene Co., Ltd.), 80% ethanol (produced by Wako Pure Chemical Industries, Ltd.)) was added, and centrifuged at 12000×G at room temperature for 1 minute to remove the solution in the tube. Then, after additional centrifugal separation at 12000×G at room temperature for 1 minute, the tube was changed to a new tube, and 25 µL of an Elution Buffer (10 mM Tris-HCl, pH8.0) (produced by Nippon Gene Co., Ltd.) was added, then centrifuged at 12000×G at room temperature for 1 minute. The resulting precipitate was dissolved in 1 µL of distilled water to recover cDNA.

It should be noted that, the same reaction as above was carried out using the same sample except for no addition of RTase (ReverTra Ace (produced by Toyobo Co., Ltd.), reverse transcriptase), in order to confirm that genomic DNA is not mixed in this experimental system.

(5) PCR Reaction

A 1 µL of cDNA obtained in the above (4) was mixed with 5 µL of distilled water, 12.5 µL of a 2×PCR Buffer for KOD FX Neo (produced by Toyobo Co., Ltd.), 4 µL of 2 mM dNTPs (produced by Toyobo Co., Ltd.), 0.5 µL (0.5 U) of KOD FX Neo (produced by Toyobo Co., Ltd.), 1 µL (10 µM) of each forward primer, and 1 µL (10 µM) of each reverse primer.

Nucleotide sequences of each primer used are as follows. The following primers are all produced by Sigma-Aldrich Corporation.

```
FOXB2 cDNA, GenBank Accession No. NM_001013735:
45-67, 201-223
                                          (SEQ ID NO: 9)
Forward primer: CTACTCTTACATCTCGCTGACCG (SEQ ID NO: 10)
Reverse primer: GAATCTTGATGAAGCAGTCGTTG
```

Amplification chain length: 179 bp

※ Forward primer of SEQ ID NO: 9 and reverse primer of SEQ ID NO: 10 were designed based on the nucleotide sequence of $45^{th}$ to $67^{th}$, and the nucleotide sequence of $201^{st}$ to $223^{rd}$ of FOXB2 cDNA, GenBank Accession No. NM_001013735, respectively. Hereinafter the same as above.

Accordingly, a region of $45^{th}$ to $223^{rd}$ of FOXB2 gene (the nucleotide sequence shown in SEQ ID NO: 1), that is a region of 179 bp (SEQ ID NO: 3) (GenBank Accession No. NM_001013735.1, position 45-223), is amplified by the nucleic acid amplification reaction using this primer pair.

```
OCT3/4 cDNA, GenBank Accession No. NM_002701:
340-361, 515-535
                                          (SEQ ID NO: 11)
Forward primer: CTTGGAGACCTCTCAGCCTGAG (SEQ ID NO: 12)
Reverse primer: CTTCAGGAGCTTGGCAAATTG
```

Amplification chain length: 196 bp

```
NANOG cDNA, GenBank Accession No. NM_024865:
284-305, 528-550
                                          (SEQ ID NO: 13)
Forward primer: CACCTATGCCTGTGATTTGTGG (SEQ ID NO: 14)
Reverse primer: CATTGAGTACACACAGCTGGGTG
```

Amplification chain length: 267 bp

```
SOX2 cDNA, GenBank Accession No. NM_003106:
31-54, 443-464
                                          (SEQ ID NO: 15)
Forward primer: GTATCAGGAGTTGTCAAGGCAGAG (SEQ ID NO: 16)
Reverse primer: CAGCTCCGTCTCCATCATGTTG
```

Amplification chain length: 434 bp

```
GAPDH cDNA, GenBank Accession No. NM_002046:
240-260, 618-638
                                          (SEQ ID NO: 17)
Forward primer: GTCACCAGGGCTGCTTTTAAC (SEQ ID NO: 18)
Reverse primer: GGCATTGCTGATGATCTTGAG
```

Amplification chain length: 399 bp

Each mixture was set in a thermal cycler, and after a reaction at 94° C. for 2 minutes, a reaction at 98° C. for 10 seconds→at 56° C. for 20 seconds→at 68° C. for 30 seconds was repeated for 28 cycles in the case of amplification of OCT3/4 cDNA, NANOG cDNA, SOX2 cDNA and FOXB2 cDNA; and for 20 cycles in the case of amplification of GAPDH cDNA, followed by a reaction at 68° C. for 2 minutes.

(6) Electrophoresis

A 5 µL of PCR amplification products obtained in the above (5), and 1 µL of a 6× x Loading Buffer Double Dye (produced by Nippon Gene Co., Ltd.) were mixed, and subjected to electrophoresis on 1.5% agarose gel. Staining was carried out using GelRed Nucleic Acid Gel Stain (produced by Wako Pure Chemical Industries, Ltd.).

It should be noted that, also as for the reaction product obtained in the above (4) by carrying out the reaction without the addition of RTase, treatment of the above (5) to (6) was carried out.

(7) Results

The results are shown collectively in FIG. 1.

As is clear from the results of FIG. 1, OCT3/4 mRNA (FIG. 1 (3)), NANOG mRNA (FIG. 1 (4)) and SOX2 mRNA (FIG. 1 (5)), which are commonly measured undifferentiation markers, were expressed in hiPS cells maintaining an undifferentiated and pluripotent state (in the case of hiPS-bFGF (+)-RTase (+)). In addition, in hiPS cells on day 5 of culture after differentiation-inducing treatment, it has also been confirmed that the markers were still expressed (band was confirmed) (in the case of hiPS-bFGF (−)-RTase of (+)). However, OCT3/4 mRNA, NANOG mRNA and SOX2 mRNA were not expressed in HDF cells which are the differentiated cells.

On the other hand, it has been confirmed that FOXB2 mRNA (FIG. 1 (1)) was expressed (band was confirmed) in hiPS cells on day 5 of culture after differentiation-inducing treatment (in the case of hiPS-bFGF (−)-RTase of (+)). However, the expression of FOXB2 mRNA was not confirmed in hiPS cells which maintained an undifferentiated and pluripotent state (in the case of hiPS-bFGF (+)-RTase (+)), nor in HDF cells which were the differentiated cells (in particular, the cells having differentiation completed).

It should be noted that, from the fact that, in the case of RTase (−), the band was not confirmed in all mRNA detection results, it has been confirmed that genomic DNA was not mixed in this experimental system.

In addition, as is clear from the detection result of GAPDH mRNA (FIG. 1 (2)), the band was confirmed in the cases of "hiPS-bFGF (+)-RTase (+)", "hiPS-bFGF (−)-RTase (+)", and "HDF-RTase (+)"; and the band was not confirmed in the cases of "hiPS-bFGF (+)-RTase (−)", "hiPS-bFGF (−)-RTase (−)", and "DF-RTase (−)". From this, it has been confirmed that mRNA was not degraded in this experimental system.

Thus, it was clarified that FOXB2 mRNA is useful as a differentiation marker, and it is capable of determining the differentiated state of cells by detecting FOXB2 mRNA. In addition, from the fact that the expression of FOXB2 mRNA was detected significantly even at a stage when change in the expression of generally measured undifferentiation markers (OCT3/4, NANOG, SOX2) has not been detected, it turned out FOXB2 mRNA is capable of determining the differentiated state of cells at an earlier stage of differentiation, as compared with conventional undifferentiation markers.

Example 2

(1) Culture and Differentiation-Inducing Treatment of Stem Cells hiPS cells (201B7 strain, Center for iPS Cell Research and Application, Kyoto University (iPS Academia Japan, Inc.)) were cultured in a medium containing or not containing bFGF (StemSure hPSC medium, produced by Wako Pure Chemical Industries, Ltd.), and the cells were recovered on day 3, day 5, and day 7 of culture.

In addition, as a comparison, HDF cells that are the differentiated cells (normal human cell-derived fibroblast, produced by Lonza Japan Co., Ltd.) were cultured in an MEM medium (+10% FBS) (produced by Wako Pure Chemical Industries, Ltd.), and the cells were recovered on day 7 of culture.

(2) Extraction of Total RNA

By a similar method as in Example 1 (2), total RNA was extracted from the each cells recovered on day 3, on day 5, and on day 7 of culture in the above (1).

In addition, as a comparison, total RNA from HMSC-bm cells (human bone marrow-derived mesenchymal stem cells) (produced by ScienCell Research Laboratories, Inc.) was used.

(3) DNase Treatment

By a similar method as in Example 1 (3), each 1 µg of total RNA and total RNA from HMSC-bm cells extracted in the above (2) was subjected to DNase treatment.

(4) Reverse Transcription Reaction

To 9.5 µL of total RNA which has been subjected to DNase treatment in the above (3), 1 µL of mixed Primer (each 5 µM) containing the following primers was added. The following primers are all produced by Sigma-Aldrich Corporation.

primer for amplification of FOXB2 mRNA, CAGAAGCTACCCTTGCCAG (SEQ ID NO: 4, GenBank Accession No. NM_001013735: 242-260), primer for amplification of OCT3/4 mRNA, GTTCTTGAAGCTAAGCTGCAG (SEQ ID NO: 5, GenBank Accession No. NM_002701: 641-661);

primer for amplification of NANOG mRNA, GTTCTGGAACCAGGTCTTCAC (SEQ ID NO: 6, GenBank Accession No. NM_024865: 631-651);

primer for amplification of SOX2 mRNA, GACCACACCATGAAGGCATTC (SEQ ID NO: 7, GenBank Accession No. NM_003106: 572-592);

primer for amplification of GAPDH mRNA, GTCTACATGGCAACTGTGAGG (SEQ ID NO: 8, GenBank Accession No. NM_002046: 1303-1323).

For each mixture, the reverse transcription reaction was carried out to recover each cDNA by a similar method as in Example 1 (4).

(5) PCR Reaction cDNA obtained in the above (4) 1 µL was mixed with 5 µL of distilled water, 12.5 µL of a 2×PCR Buffer for KOD FX Neo (produced by Toyobo Co., Ltd.), 4 µL of 2 mM dNTPs (produced by Toyobo Co., Ltd.), 0.5 µL (0.5 U) of KOD FX Neo (produced by Toyobo Co., Ltd.), 1 µL (10 µM) of each forward primer, and 1 µL (10 µM) of each reverse primer.

Nucleotide sequences of each primer used are as follows. The following primers are all produced by Sigma-Aldrich Corporation.

```
FOXB2 cDNA, GenBank Accession No. NM_001013735:
45-67, 201-223
                                       (SEQ ID NO: 9)
Forward primer: CTACTCTTACATCTCGCTGACCG (SEQ ID NO: 10)
Reverse primer: GAATCTTGATGAAGCAGTCGTTG
```

Amplification chain length: 179 bp

```
OCT3/4 cDNA, GenBank Accession No. NM_002701:
340-361, 515-535
                                       (SEQ ID NO: 11)
Forward primer: CTTGGAGACCTCTCAGCCTGAG (SEQ ID NO: 12)
Reverse primer: CTTCAGGAGCTTGGCAAATTG
```

Amplification chain length: 196 bp

```
NANOG cDNA, GenBank Accession No. NM_024865:
284-305, 528-550
                                       (SEQ ID NO: 13)
Forward primer: CACCTATGCCTGTGATTTGTGG (SEQ ID NO: 14)
Reverse primer: CATTGAGTACACACAGCTGGGTG
```

Amplification chain length: 267 bp

```
SOX2 cDNA, GenBank Accession No. NM_003106:
31-54, 443-464
                                       (SEQ ID NO: 15)
Forward primer: GTATCAGGAGTTGTCAAGGCAGAG (SEQ ID NO: 16)
Reverse primer: CAGCTCCGTCTCCATCATGTTG
```

Amplification chain length: 434 bp

```
GAPDH cDNA, GenBank Accession No. NM_002046:
240-260, 618-638
                                       (SEQ ID NO: 17)
Forward primer: GTCACCAGGGCTGCTTTTAAC (SEQ ID NO: 18)
Reverse primer: GGCATTGCTGATGATCTTGAG
```

Amplification chain length: 399 bp

Each mixture was set in a thermal cycler, and after a reaction at 94° C. for 2 minutes, a reaction at 98° C. for 10 seconds→at 56° C. for 20 seconds→at 68° C. for 30 seconds was repeated for 28 cycles in the case of amplification of OCT3/4 cDNA, NANOG cDNA, SOX2 cDNA, and FOXB2 cDNA; and for 20 cycles in the case of amplification of GAPDH cDNA, followed by a reaction at 68° C. for 2 minutes.

(6) Electrophoresis

5 µL of PCR amplification products and 1 µL of a 6× Loading Buffer Double Dye (produced by Nippon Gene Co., Ltd.) were mixed, and subjected to electrophoresis on 1.5% agarose gel. Staining was carried out using GelRed Nucleic Acid Gel Stain (produced by Wako Pure Chemical Industries, Ltd.).

It should be noted that, also for the reaction product obtained in the above (4) by carrying out the reaction without the addition of RTase, treatment of the above (5) to (6) was carried out.

(7) Results

The results are shown collectively in FIG. 2.

As is clear from the results shown in FIG. 2, when hiPS cells were subjected to differentiation-inducing treatment by culturing in a bFGF-free medium, the expression level of FOXB2 mRNA was increased in proportion to increase in culture period.

In contrast, it has been confirmed that, even when differentiation-inducing treatment was given by culturing in a bFGF-free medium, well-known undifferentiation markers other than FOXB2 mRNA (OCT3/4 mRNA, NANOG mRNA, SOX2 mRNA, GAPDH mRNA) were still expressed without fading, up to the day 7 of culture after differentiation-inducing treatment.

On the other hand, when HMSC-bm (human bone marrow-derived mesenchymal stem cells) was cultured in the bFGF-free medium, the expression of FOXB2 mRNA nor the expression of known undifferentiation markers (the OCT3/4 mRNA, NANOG mRNA, the SOX2 mRNA, GAPDH mRNA) were not confirmed. HMSC-bm is the somatic stem cells formed from the stem cells (RS cells) through the mesoderm. From this fact, it is presumed that when differentiation of the undifferentiated stem cells would have developed to this level, FOXB2 mRNA is no longer expressed, in other words, FOXB2 mRNA is expressed specifically at an early stage of differentiation of cells.

In addition, the expression of FOXB2 mRNA and the expression of known undifferentiation markers (OCT3/4 mRNA, NANOG mRNA, SOX2 mRNA, GAPDH mRNA) were not confirmed in HDF cells of the day 5 of culture.

It should be noted that, from the fact that, in the case of RTase (−), the band was not observed in all mRNA detection results, it has been confirmed that the genomic DNA was not mixed in this experimental system. In addition, since GAPDH mRNA was detected in all cases of RTase (+), it has been confirmed that mRNA was not degraded in this experimental system, and the expression of mRNA has been detected correctly.

As is clear from the results, the expression of FOXB2 mRNA was detected earlier than change in the expression of commonly measured undifferentiation markers (OCT3/4, NANOG, SOX2) was detected. From the fact described above, it was clarified that FOXB2 mRNA is particularly useful as a differentiation marker for an early stage of differentiation of cells, in other words, by detection of the expression of FOXB2 mRNA, the differentiated state of cells can be determined at an early stage of differentiation.

Example 3

(1) Culture and Differentiation-Inducing Treatment of Stem Cells hiPS cells (201B7 strain, Center for iPS Cell Research and Application, Kyoto University (iPS Academia Japan, Inc.)), and as a comparison, HDF cells that are the differentiated cells (normal human cell-derived fibroblast, produced by Lonza Japan Co., Ltd.) were subcultured for three times in a medium containing or not containing bFGF (100 ng/mL) (StemSure hPSC medium, produced by Wako Pure Chemical Industries, Ltd.), and the cells were recovered on day 6 of culture.

(2) Extraction of Total RNA

Using a kit ISOGEN (manufactured by Nippon Gene Co., Ltd.) which is a commercially available nucleic acid extraction reagent, and according to the product instruction, total RNA was extracted from the cells recovered in the above (1).

(3) DNase Treatment

By a similar method as in Example 1 (3), 1 μg of total RNA extracted in the above (2) was each subjected to DNase treatment.

(4) Reverse Transcription Reaction

To a 9.5 μL of total RNA which has been subjected to DNase treatment in the above (3), 1 μL of mixed Primer (each 5 μM) containing amplification primers targeting the following each mRNA was added. The following primers are all produced by Sigma-Aldrich Corporation.

primer for amplification of FOXB2 mRNA, CAGAAGC-TACCCTTGCCAG (SEQ ID NO: 4, GenBank Accession No. NM_001013735: 242-260), primer for amplification of OCT3/4 mRNA, GTTCTT-GAAGCTAAGCTGCAG (SEQ ID NO: 5, GenBank Accession No. NM_002701: 641-661);

primer for amplification of NANOG mRNA, GTTCTG-GAACCAGGTCTTCAC (SEQ ID NO: 6, GenBank Accession No. NM_024865: 631-651);

primer for amplification of SOX2 mRNA, GACCACAC-CATGAAGGCATTC (SEQ ID NO: 7, GenBank Accession No. NM_003106: 572-592);

primer for amplification of FGF5 mRNA, CTCCCT-GAACTTGCAGTCATC (SEQ ID NO: 19, GenBank Accession No. NM_004464: 709-729);

primer for amplification of CDX2 mRNA, CCTGAG-GAGTCTAGCAGAGTC (SEQ ID NO: 20, GenBank Accession No. NM_001265: 1359-1379);

primer for amplification of GATA4 mRNA, GAT-TACGCAGTGATTATGTCCC (SEQ ID NO: 21, GenBank Accession No. NM_001308094: 1110-1131);

primer for amplification of GATA6 mRNA, CATCTT-GACCCGAATACTTGAG (SEQ ID NO: 22, GenBank Accession No. NM_005257: 1961-1982)

primer for amplification of SOX17 mRNA, CCCAG-GAGTCTGAGGATTTCC (SEQ ID NO: 23, GenBank Accession No. NM_022454: 1515-1535)

primer for amplification of GAPDH mRNA, GTCTA-CATGGCAACTGTGAGG (SEQ ID NO: 8, GenBank Accession No. NM_002046: 1303-1323)

Each mixture was incubated at 72° C. for 3 minutes, then immediately cooled with ice. Then, 4 μL of a 5× Buffer (produced by Toyobo Co., Ltd.), 4 μL of 2.5 mM dNTPs (produced by Nippon Gene Co., Ltd.), 0.5 μL (20 U) of an RNase Inhibitor, super (produced by Wako Pure Chemical Industries, Ltd.), and 1 μL (100 U) of ReverTra Ace (Toyobo Co., Ltd.) were added thereto and mixed, and incubated at 42° C. for 50 minutes. Thereafter, 100 μL of a Binding Buffer (5.5 M guanidine hydrochloride (produced by Wako Pure Chemical Industries, Ltd.), 20 mM Tris-HCl, pH 6.6 (produced by Wako Pure Chemical Industries, Ltd.)) was added and mixed, then transferred to an Econospin (manufactured by GeneDesign, Inc.) and centrifuged at 12000×G at room temperature for 1 minute to remove the solution in the tube. Subsequently, 500 μL of a Washing Buffer (2 mM Tris-HCl, pH 7.5 (Nippon Gene Co., Ltd.), and 80% ethanol (produced by Wako Pure Chemical Industries, Ltd.)) was added, and centrifuged at 12000×G at room temperature for 1 minute to remove the solution in the tube. Then, after additional centrifugal separation at 12000×G at room temperature for 1 minute, the tube was changed to a new tube, and 25 μL of an Elution Buffer (10 mM Tris-HCl pH8.0) (produced by Nippon Gene Co., Ltd.) was added, then centrifuged at 12000×G at room temperature for 1 minute, and the resulting precipitate was dissolved in 1 μL of distilled water to recover cDNA.

(5) PCR Reaction cDNA obtained in the above (4) 1 μL was mixed with 5 μL of distilled water, 12.5 μL of a 2×PCR Buffer for KOD FX Neo (produced by Toyobo Co., Ltd.), 4 μL of 2 mM dNTPs (produced by Toyobo Co., Ltd.), 0.5 μL (0.5 U) of KOD FX Neo (produced by Toyobo Co., Ltd.), 1 μL (10 μM) of each forward primer, and 1 μL (10 μM) of each reverse primer.

Nucleotide sequences of each primer used are as follows. The following primers are all produced by Sigma-Aldrich Corporation.

FOXB2 cDNA, GenBank Accession No. NM_001013735: 45-67, 201-223

(SEQ ID NO: 9)
Forward primer: CTACTCTTACATCTCGCTGACCG (SEQ ID NO: 10)
Reverse primer: GAATCTTGATGAAGCAGTCGTTG Amplification chain length: 179 bp OCT3/4 cDNA, GenBank Accession No. NM_002701: 340-361, 515-535

(SEQ ID NO: 11)
Forward primer: CTTGGAGACCTCTCAGCCTGAG (SEQ ID NO: 12)
Reverse primer: CTTCAGGAGCTTGGCAAATTG Amplification chain length: 196 bp NANOG cDNA, GenBank Accession No. NM_024865: 284-305, 528-550

(SEQ ID NO: 13)
Forward primer: CACCTATGCCTGTGATTTGTGG (SEQ ID NO: 14)
Reverse primer: CATTGAGTACACACAGCTGGGTG Amplification chain length: 267 bp SOX2 cDNA, GenBank Accession No. NM_003106: 31-54, 443-464
Forward primer:
(SEQ ID NO: 15)
GTATCAGGAGTTGTCAAGGCAGAG Reverse primer:
(SEQ ID NO: 16)
CAGCTCCGTCTCCATCATGTTG Amplification chain length: 434 bp FGF5 cDNA, GenBank Accession No. NM_004464: 462-482, 615-637
Forward primer:
(SEQ ID NO: 24)
GCAGAGCAGTTTCCAGTGGAG Reverse primer:
(SEQ ID NO: 25)
GTATTCCTACAATCCCCTGAGAC Amplification chain length: 176 bp CDX2 cDNA, GenBank Accession No. NM_001265: 923-944, 1176-1196
Forward primer:
(SEQ ID NO: 26)
CAAATATCGAGTGGTGTACACG Reverse primer:
(SEQ ID NO: 27)
GACACTTCTCAGAGGACCTGG Amplification chain length: 274 bp GATA4 cDNA, GenBank Accession No. NM_001308094: 795-816, 1020-1040
Forward primer:
(SEQ ID NO: 28)
CAGCTCCTTCAGGCAGTGAGAG Reverse primer:
(SEQ ID NO: 29)
CGGGAGACGCATAGCCTTGTG Amplification chain length: 246 bp GATA6 cDNA, GenBank Accession No. NM_005257: 1682-1703, 1842-1864
Forward primer:
(SEQ ID NO: 30)
GCTTGTGGACTCTACATGAAAC Reverse primer:
(SEQ ID NO: 31)
GCTGCAATCATCTGAGTTAGAAG Amplification chain length: 183 bp SOX17 cDNA GenBank Accession No. NM_022454: 1286-1306, 1490-1511
Forward primer:
(SEQ ID NO: 32)
CGGAATTTGAACAGTATCTGC Reverse primer:
(SEQ ID NO: 33)
GCTCCTCCAGGAAGTGTGTAAC Amplification chain length: 226 bp GAPDH cDNA, GenBank Accession No. NM_002046: 240-260, 618-638
Forward primer:
(SEQ ID NO: 17)
GTCACCAGGGCTGCTTTTAAC Reverse primer:
(SEQ ID NO: 18)
GGCATTGCTGATGATCTTGAG Amplification chain length: 399 bp Each mixture was set in a thermal cycler, and after a reaction at 94° C. for 2 minutes, a reaction at 98° C. for 10 seconds→at 56° C. for 20 seconds→at 68° C. for 30 seconds was repeated for 24 cycles in the case of amplification of OCT3/4 cDNA, NANOG cDNA and SOX2 cDNA; and for 28 cycles in the case of amplification of FOXB2 cDNA, FGF5 cDNA, GATA4 cDNA, GATA6 cDNA and SOX17 cDNA; and for 20 cycles in the case of amplification of GAPDH cDNA, followed by a reaction at 68° C. for 2 minutes.

(6) Electrophoresis

A 5 µL of PCR amplification products obtained in the above (5), and 1 µL of a 6× Loading Buffer Double Dye (produced by Nippon Gene Co., Ltd.) were mixed, and subjected to electrophoresis on 1.5% agarose gel. Staining was carried out using GelRed Nucleic Acid Gel Stain (produced by Wako Pure Chemical Industries, Ltd.).

It should be noted that, also for the reaction product obtained in the above (4) by carrying out a reaction without the addition of RTase, treatment of the above (5) to (6) was carried out.

(7) Result

The results are shown collectively in FIG. 3.

As is clear from the results shown in FIG. 3, it has been confirmed that, when hiPS cells were subjected to differentiation-inducing treatment by culturing in a bFGF-free medium, even on day 6 of culture after differentiation-inducing treatment (in the case of hiPS-bFGF (−)-RTase (+)), the undifferentiation markers of OCT3/4 mRNA, NANOG mRNA and SOX2 mRNA were still expressed (band was confirmed).

In addition, it has been confirmed that in hiPS cells on day 6 of culture after differentiation-inducing treatment, known differentiation markers of FGF5 mRNA (ectoderm differentiation marker), CDX2 mRNA (ectoderm differentiation marker), GATA4 mRNA (endoderm differentiation marker), GATA6 mRNA (endoderm differentiation marker), SOX7 mRNA (endoderm differentiation marker), and SSEA-1 mRNA (differentiation marker) were not yet expressed (band was not observed).

On the other hand, it has been confirmed that in hiPS cells on day 6 of culture after differentiation-inducing treatment (in the case of hiPS-bFGF (−)-RTase (+)), FOXB2 mRNA was expressed (band was confirmed).

It should be noted that, from the fact that, in the case of RTase (−), the band was not observed in all mRNA detection results, it has been confirmed that genomic DNA was not mixed in this experimental system.

In addition, as is clear from the detection result of GAPDH mRNA, the band was confirmed in the cases of "hiPS-bFGF (+)-RTase (+)", "hiPS-bFGF (−)-RTase (+)", and "HDF-RTase (+)"; and the band was not confirmed in the cases of "hiPS-bFGF (+)-RTase (−)", "hiPS-bFGF (−)-RTase (−)", and "DF-RTase (−)". From this, it has been confirmed that mRNA was not degraded in this experimental system.

Thus, it was clarified that FOXB2 mRNA is useful as a differentiation marker, and by detection of FOXB2 mRNA, it is capable of determining the differentiated state of cells. In addition, even at a stage when change in the expression of general undifferentiation markers (OCT3/4, NANOG, SOX2) have not been detected, the expression of FOXB2 mRNA was detected significantly.

Further, at a stage when FGF5 mRNA, which is currently known as the most promising differentiation marker, has not yet expressed, the expression of FOXB2 mRNA was detected. That is, it turned out that FOXB2 mRNA is capable of determining the differentiated state of cells at an earlier stage (initial stage) of differentiation, as compared with conventional differentiation markers and undifferentiation markers.

From the above results, it has been clarified that FOXB2 mRNA is a quite useful differentiation marker, as compared with conventional differentiation markers/undifferentiation markers. In addition, since determination of the differentiated cells can be carried out at an early stage of cell culture, FOXB2 is useful for an early stage screening of cells or quality control of stem cells, and reduction in culturing period and cost reduction in expenditure regarding culture medium, or the like, can be expected.

Example 4

Mouse ES cells were subjected to differentiation-inducing treatment by culturing in a LIF-free medium, and the expression of Foxb2 mRNA and known undifferentiation markers were detected by RT-PCR method.

(1) Culture and Differentiation-Inducing Treatment of Stem Cells mES cells (D3 strain, ATCC, b723512) were subcultured for three times in a medium containing or not containing LIF (1000 unit) (StemSure DMEM, StemSure Serum replacement, an MEM non-essential amino acid solution, an L-glutamine solution, a StemSure 2-mercaptoethanol solution, produced by Wako Pure Chemical Industries, Ltd.), and the cells were recovered on day 3, day 5, and day 7 of culture.

(2) Extraction of Total RNA

Using a kit ISOGEN (manufactured by Nippon Gene Co., Ltd.) which is a commercially available nucleic acid extraction reagent, and according to the product instruction, total RNA was extracted from the cells recovered in the above (1).

(3) DNase Treatment

To 1 µg of total RNA extracted in the above (2), distilled water was added to make a total volume of 17 µL, then 2 µL of a 10×Reaction Buffer (produced by Promega Corporation) and 1 µL (1 U) of RQ1 RNase-Free DNase (produced by Promega Corporation) were added and mixed, and incubated at 37° C. for 20 minutes. After that, 1 µL of a Stop Buffer (20 mM EGTA) (produced by Promega Corporation) was added and mixed, then incubated at 65° C. for 10 minutes. Thereafter, 100 µL of a Binding Buffer (5.5 M guanidine hydrochloride (produced by Wako Pure Chemical Industries, Ltd.), 20 mM Tris-HCl, pH 6.6) was added to the reactant and mixed, then transferred to an Econospin (silica membrane spin column for nucleic acid purification, manufactured by GeneDesign, Inc.), and centrifuged at 12000×G at room temperature for 1 minute to remove the solution in the tube. Subsequently, 500 µL of a Washing Buffer (2 mM Tris-HCl, pH 7.5 (produced by Nippon Gene Co., Ltd.), 80% ethanol (produced by Wako Pure Chemical Industries, Ltd.)) was added to the Econospin, and centrifuged at 12000×G at room temperature for 1 minute to remove the solution in the tube. Then, after additional centrifugal separation at 12000×G at room temperature for 1 minute, the tube was changed to a new tube, and 50 µL of an Elution Buffer (10 mM Tris-HCl, pH 8.0, manufactured by Nippon Gene Co., Ltd.) was added, then centrifuged at 12000×G at room temperature for 1 minute to recover total RNA. Thereafter, ethanol precipitation was carried out, and the resulting precipitate was dissolved in 9.5 µL of distilled water.

(4) Reverse Transcription Reaction

To 9.5 µL of total RNA which has been subjected to DNase treatment in the above (3), 1 µL of mixed Primer (each 5 µM) containing amplification primers targeting the following each mRNA was added. The following primers are all produced by Sigma-Aldrich Corporation.

primer for amplification of Foxb2 mRNA, CATGAT-GAACTTGTAGATGTC (SEQ ID NO: 37, GenBank Accession No. NM_008023: 302-322);

primer for amplification of Oct3/4 mRNA, CATGTTCT-TAAGGCTGAGCTGC (SEQ ID NO: 38, GenBank Accession No. NM_013633: 617-638);

primer for amplification of Nanog mRNA, CTGAATCAGACCATTGCTAGTC (SEQ ID NO: 39, GenBank Accession No. NM_028016: 388-408);

primer for amplification of Sox2 mRNA, CAACGATATCAACCTGCATGG (SEQ ID NO: 40, GenBank Accession No. NM_011443: 2120-2140);

primer for amplification of Klf2 mRNA, GAACTGGTGGCAGAGTCATTTTC (SEQ ID NO: 41, GenBank Accession No. NM_008452: 1205-1227);

primer for amplification of Esrrb mRNA, GATTCGAGACGATCTTAGTCAATG (SEQ ID NO: 42, GenBank Accession No. NM_011934: 957-980);

An amplification primer of Fgf5 mRNA, GACGCATAGGTATTATAGCTG (SEQ ID NO: 43, GenBank Accession No. NM_010203: 729-749);

An amplification primer of Gapdh mRNA, CTTGATGTCATCATACTTGGC (SEQ ID NO: 44, GenBank Accession No. NM_001289726: 843-863).

Each mixture was incubated at 72° C. for 3 minutes, then immediately cooled with ice. Then, 4 μL of a 5× Buffer (produced by Toyobo Co., Ltd.), 4 μL of 2.5 mM dNTPs (produced by Nippon Gene Co., Ltd.), 0.5 μL (20 U) of an RNase Inhibitor, super (produced by Wako Pure Chemical Industries, Ltd.), and 1 μL (100 U) of ReverTra Ace (Toyobo Co., Ltd.) were added thereto and mixed, and incubated at 42° C. for 50 minutes. Thereafter, 100 μL of a Binding Buffer (5.5 M guanidine hydrochloride (produced by Wako Pure Chemical Industries, Ltd.), 20 mM Tris-HCl, pH 6.6 (produced by Wako Pure Chemical Industries, Ltd.)) was added and mixed, then transferred to the Econospin (manufactured by GeneDesign, Inc.) and centrifuged at 12000×G at room temperature for 1 minute to remove the solution in the tube. Subsequently, 500 μL of a Washing Buffer (2 mM Tris-HCl, pH 7.5 (produced by Nippon Gene Co., Ltd.), 80% ethanol (produced by Wako Pure Chemical Industries, Ltd.)) as added, and centrifuged at 12000×G at room temperature for 1 minute to remove the solution in the tube. Then, after additional centrifugal separation at 12000×G at room temperature for 1 minute, the tube was transferred to a new tube, and 25 μL of an Elution Buffer (10 mM Tris-HCl pH8.0 (produced by Nippon Gene Co., Ltd.)) was added, then centrifuged at 12000×G at room temperature for 1 minute, and the resulting precipitate was dissolved in 1 μL of distilled water to recover cDNA.

(5) PCR Reaction

1 μL of cDNA obtained in the above (4) was mixed with 5 μL of distilled water, 12.5 μL of a 2×PCR Buffer for KOD FX Neo (produced by Toyobo Co., Ltd.), 4 μL of 2 mM dNTPs (produced by Toyobo Co., Ltd.), 0.5 μL (0.5 U) of KOD FX Neo (produced by Toyobo Co., Ltd.), 1 μL (10 μM) of each forward primer, and 1 μL (10 μM) of each reverse primer.

Nucleotide sequences of each primer used are as follows. The following primers are all produced by Sigma-Aldrich Corporation.

```
Foxb2 cDNA, GenBank Accession No. NM_008023:
132-152, 279-300
Forward primer:
                                        (SEQ ID NO: 45)
CTTTCCAAGAGGCGTTAAGGC Reverse primer:
                                        (SEQ ID NO: 46)
CTCAGAGGCAGCATCTTCTCAG
```

Amplification chain length: 169 bp

```
Oct3/4 cDNA, GenBank Accession No. NM_013633:
163-186, 480-501
Forward primer:
                                        (SEQ ID NO: 47)
GAACCTGGCTAAGCTTCCAAG Reverse primer:
                                        (SEQ ID NO: 48)
GCTTGGCAAACTGTTCTAGCTC
```

Amplification chain length: 339 bp

```
Nanog cDNA, GenBank Accession No. NM_028016:
110-134, 388-408
Forward primer:
                                        (SEQ ID NO: 49)
GCATTAGACATTTAACTCTTCTTTC Reverse primer:
                                        (SEQ ID NO: 50)
CTTGAAGAGGCAGGTCTTCAG
```

Amplification chain length: 299 bp

```
Sox2 cDNA, GenBank Accession No. NM_011443:
1652-1674, 1836-1859
Forward primer:
                                        (SEQ ID NO: 51)
GAATCGGACCATGTATAGATCTG Reverse primer:
                                        (SEQ ID NO: 52)
CATTTGATTGCCATGTTTATCTCG
```

Amplification chain length: 208 bp

```
Klf2 cDNA, GenBank Accession No. NM_008452:
910-931, 1159-1182
Forward primer:
                                        (SEQ ID NO: 53)
GAAGCCTTATCATTGCAACTGG Reverse primer:
                                        (SEQ ID NO: 54)
CTGTCCTAAGGTCCAATAAATAGC
```

Amplification chain length: 273 bp

```
Esrrb cDNA, GenBank Accession No. NM_011934:
552-573, 760-782
Forward primer:
                                        (SEQ ID NO: 55)
GCAAGAGCTACGAGGACTGTAC Reverse primer:
                                        (SEQ ID NO: 56)
GTTTGGTGATCTCACATTCATTG
```

Amplification chain length: 231 bp

```
Fgf5 cDNA, GenBank Accession No. NM_010203:
445-465, 617-639
Forward primer:
                                        (SEQ ID NO: 57)
GAACATAGCAGTTTCCAGTGG Reverse primer:
                                        (SEQ ID NO: 58)
GTTGCTGAAAACTCCTCGTATTC
```

Amplification chain length: 195 bp

```
Gapdh cDNA, GenBank Accession No. NM_001289726:
224-246, 512-534
Forward primer:
                                          (SEQ ID NO: 59)
GTTCCAGTATGACTCCACTCACG Reverse primer:
                                          (SEQ ID NO: 60)
CATTGCTGACAATCTTGAGTGAG
```

Amplification chain length: 311 bp

Each mixture was set in a thermal cycler, and after a reaction at 94° C. for 2 minutes, a reaction at 98° C. for 10 seconds→at 57° C. for 20 seconds→at 68° C. for 30 seconds was repeated for 25 cycles in the case of amplification of Oct3/4 cDNA, Nanog cDNA, the Sox2 cDNA, Klf2 cDNA, and Esrrb cDNA; for 30 cycles in the case of amplification of Fgf5 cDNA and Foxb2 cDNA; and for 20 cycles in the case of amplification of Gapdh cDNA, followed by a reaction at 68° C. for 2 minutes.

(6) Electrophoresis

A 5 μL of PCR amplification products obtained in the above (5), and 1 μL of a 6× Loading Buffer Double Dye (produced by Nippon Gene Co., Ltd.) were mixed, and subjected to electrophoresis on 1.5% agarose gel. Staining was carried out using GelRed Nucleic Acid Gel Stain (produced by Wako Pure Chemical Industries, Ltd.).

It should be noted that, also for the reaction product obtained in the above (4) by carrying out the reaction without the addition of RTase, treatment of the above (5) to (6) was carried out.

(7) Results

The results are shown collectively in FIG. 4.

As is clear from the results shown in FIG. 4, it has been confirmed that FOXB2 mRNA was expressed (band was confirmed) in ES cells on day 7 of culture after differentiation-inducing treatment (in the case of LIF (−)-RTase (+)). However, Foxb2 mRNA was not expressed in ES cells maintaining an undifferentiated and pluripotent state (in the case of LIF (+)-RTase (+)).

It has been confirmed that Fgf5 mRNA, which is a differentiation marker, was expressed (band was confirmed) in ES cells on day 7 of culture after differentiation-inducing treatment (in the case of LIF (−)-RTase (+)).

In addition, undifferentiation markers of Oct3/4 mRNA, Nanog mRNA and Sox2 mRNA were expressed in ES cells maintaining an undifferentiated and pluripotent state (in the case of LIF (+)-RTase (+)). In addition, in ES cells on day 7 of culture after differentiation-inducing treatment (in the case of LIF (−)-RTase (+)), the expression was still confirmed (band was confirmed).

It should be noted that, from the fact that, in the case of RTase (−), the band was not observed in all mRNA detection results, it has been confirmed that genomic DNA was not mixed in this experimental system.

In addition, as is clear from the detection result of Gapdh mRNA, the band was confirmed in the cases of "LIF (+)-RTase (+)" and "LIFF (−)-RTase (+)"; and the band was not confirmed in the cases of "LIF (+)-RTase (−)", and "LIF (−)-RTase (−)". It has been confirmed from this that mRNA was not degraded in this experimental system.

As is clear from the results, the expression of Foxb2 mRNA was detected at an early stage comparable to the Fgf5 mRNA which is currently known most promising as a differentiation marker. In addition, the expression of Foxb2 mRNA was detected significantly, even at a stage when change in the expression of general undifferentiation markers (Oct3/4, Nanog, Sox2) has not been detected. Further, at a stage of day 7 of culture after induction of differentiation where Klf2 mRNA or Esrrb mRNA, which is known as a naive marker, is not yet disappeared, the expression of Foxb2 mRNA was confirmed.

From the facts described above, it has been understood that Foxb2 mRNA is capable of determining the differentiated state of ES cells at an earlier stage of differentiation, as compared with conventional undifferentiation markers. Moreover, since determination of differentiated cells can be carried out at an early stage of culture, it is useful for an early stage screening of cells, and for quality control of stem cells, and reduction in culturing period and cost reduction in expenditure regarding culture medium, or the like, can be expected.

Reference Example 1: Confirmation of the Differentiated State of the Cells (1) Culture and Differentiation-Inducing Treatment of the Stem Cells hiPS cells (201B7 strain, Center for iPS Cell Research and Application, Kyoto University (iPS Academia Japan, Inc.) were cultured in the following medium.

hiPS cells were seeded in a hPSC A medium with or without the addition of +bFGF and +ROCK inhibitors (produced by Wako Pure Chemical Industries, Ltd.) in 4 plates of wells, so as to provide 20000 cells/well, and cultured for one day.

From the 2nd day of culture, the mediums of (1) hPSCΔ medium−bFGF, and (2) hPSCΔ medium+bFGF (100 mg/mL) were assigned to each 2 sets of 4 plates of wells, and each medium was changed daily. After 6th day of culture, the cells were observed.

(2) Results

The results are shown in FIG. 5.

In FIG. 5, (1) is a photograph of hiPS cells cultured in the bFGF-free medium (differentiation-inducing treatment). (2) is a photograph of hiPS cells cultured in the bFGF-added medium.

It has been known that when hiPS cells are cultured in the bFGF-free medium, iPS cells will be induced to differentiate into cells of neuronal lineage.

As is clear from FIG. 5 (1), when cultured in the bFGF-free (−bFGF) medium, it has been confirmed that morphology of the cells on day 6 of culture has changed to a protruding or fibrous state (colony edge is jagged.).

However, as is clear from FIG. 5 (2), when cultured in the bFGF-added (+bFGF) medium, such a change in cell morphology was not observed, as observed when cultured in the bFGF-free medium.

From the above, it has been confirmed that when cultured in the bFGF-free medium, differentiation of hiPS cells is induced.

Experimental Example 1: Detection of FOXB2 Protein-1

1) Preparation of an Anti-Human FOXB2 Protein Antibody-Immobilized Microplate for ELISA A solution of the anti-human FOXB2 protein antibody (50 mM MOPS buffer solution (pH 7.0)) is dispensed into each well of the microplate for ELISA (manufactured by Nunk Co., Ltd.), and allowed to stand for 24 hours to obtain the anti-human FOXB2 protein antibody-immobilized microplate for ELISA.

2) Preparation of a Peroxidase-Labeled Anti-FOXB2 Protein Antibody

The anti-human FOXB2 protein antibody is labeled with a peroxidase by a common method.

3) Sample Preparation hiPS cells on day 3 of culture after induction of differentiation are recovered and destroyed by sonication to obtain a cell lysate. The resulting lysate is dissolved in a buffer solution, to be used as a sample.

4) Measurement

The sample prepared in the above 3) is added to each well of the anti FOXB2 protein antibody-immobilized microplate for ELISA prepared in the above 1), and subjected to a reaction at 37° C. for about 1 hour. Then, each well is washed with the buffer solution several times.

The peroxidase-labeled anti-FOXB2 protein antibody prepared in the above 2) is dispensed into each well, and subjected to a reaction at 37° C. for about 1 hour. Each well is washed with the buffer solution and subsequently with distilled water, and each 50 μL of a TMB (3,3',5,5'-tetramethylbenzidine) solution (produced by Wako Pure Chemical Industries, Ltd.) is added to each well, and subjected to a reaction at 25° C. for 30 minutes. Thereafter, each of 50 μL of a reaction stop solution (1 M phosphoric acid solution) is added to each well to stop the reaction. Absorbance at 450 nm is measured using a Vmax (manufactured by Molecular Devices Corp.).

As a result, when FOXB2 protein is detected, it is determined that hiPS cells used as the sample are in the differentiated state. Alternatively, it is determined that in the cell population of hiPS cells used as the sample, cells in the differentiated state are contained Experimental Example 2: Detection of FOXB2 Protein-2

1) Sample Preparation hiPS cells on day 3 of culture after induction of differentiation are recovered and destroyed by sonication to obtain a cell lysate. The resulting lysate is dissolved in a buffer solution, to be used as a sample.

2) Preparation of a Peroxidase-Labeled Anti-FOXB2 Protein Antibody

The anti-human FOXB2 protein antibody is labeled with a peroxidase by a common method.

3) Western Blotting

The resulting sample in the above 1) is applied on SuperSep™ (an electrophoresis gel, manufactured by Wako Pure Chemical Industries, Ltd., 5 to 20% gradient gel), and subjected to SDS-PAGE electrophoresis (under a constant current of 25 mA). Then, fractions after electrophoresis are transferred to a PVDF membrane by a semi-dry blotting method.

Block Ace (produced by DS Pharma Biomedical Co., Ltd.) is dissolved in PBS-T (Phosphate Buffered Saline with Tween™ 20, pH 7.4) to prepare a blocking solution. The PVDF membrane after the transfer is immersed in the blocking solution and subjected to blocking treatment at room temperature for 1 hour, then the PVDF membrane is washed, and immersed in the blocking solution.

Subsequently, the resulting peroxidase-labeled anti-human FOXB2 protein antibody obtained in the above 2) is added to the blocking solution, and immersed at room temperature for about 1 hour. The PVDF membrane is washed, and luminescence is generated by an ECL™ Prime Western Blotting Detection Reagent (a chemiluminescent substrate of a peroxidase, produced by GE Healthcare), and detection is carried out using LAS4000 (manufactured by Fujifilm Corporation) in an exposure time of 10 seconds.

As a result, when FOXB2 protein is detected, it is determined that hiPS cells used as a sample are in the differentiated state. Alternatively, it is determined that in the cell population of hiPS cells used as a sample, cells in the differentiated state are contained.

INDUSTRIAL APPLICABILITY

According to the present invention, differentiated state of stem cells can be determined at an early stage of differentiation. In addition, the present invention is applicable to quality control of stem cells, and to preparation and isolation methods of differentiated cells. Further, since the present invention is capable of determining differentiated cells at an early stage of culture, the present invention is useful for an early stage screening of cells, or for quality control of stem cells, and reduction in culturing period and cost reduction in expenditure regarding culture medium, or the like, can be expected.

The invention claimed is:

1. A method for preparing differentiated stem cells comprising:
   (a) subjecting undifferentiated stem cells to differentiation-inducing treatment,
   (b) detecting an expression of FOXB2 gene in the stem cells, and
   (c) isolating the stem cells in which the expression of FOXB2 gene is detected.

2. The method according to claim 1, wherein the detecting of expression of FOXB2 gene is carried out by detecting FOXB2 mRNA.

3. The method according to claim 1, wherein the detecting of expression of FOXB2 gene is carried out by detecting FOXB2 protein.

4. The method according to claim 2, wherein the FOXB2 mRNA is selected from the group consisting of:
   (1) mRNA having a nucleotide sequence shown in SEQ ID NO: 1 or SEQ ID NO: 34,
   (2) mRNA having a nucleotide sequence which has a sequence homology of 97% or more to the nucleotide sequence shown in SEQ ID NO: 1 or SEQ ID NO: 34,
   (3) mRNA encoding an amino acid sequence shown in SEQ ID NO: 2 or SEQ ID NO: 35,
   (4) mRNA encoding an amino acid sequence in which 1-3 amino acids in the amino acid sequence shown in SEQ ID NO: 2 or SEQ ID NO: 35 are deleted, inserted, substituted, or added, and
   (5) mRNA encoding an amino acid sequence which has a sequence homology of 97% or more to the amino acid sequence shown in SEQ ID NO: 2 or SEQ ID NO: 35.

5. The method according to claim 3, wherein the FOXB2 protein is selected from the group consisting of:
   (1) a protein having an amino acid sequence shown in SEQ ID NO: 2 or SEQ ID NO: 35,
   (2) a protein having an amino acid sequence shown in SEQ ID NO: 2 or SEQ ID NO: 35 in which 1-3 amino acids are deleted, inserted, substituted, or added, and (3) a protein having an amino acid sequence which has a sequence homology of 97% or more to the amino acid sequence shown in SEQ ID NO: 2 or SEQ ID NO: 35.

6. The method according to claim 2, wherein the detecting of FOXB2 mRNA is carried out by an RT-PCR method.

7. The method according to claim 1, wherein the undifferentiated stem cells are iPS cells or ES cells.

8. The method according to claim 1, wherein an amount of expression of FOXB2 gene in the stem cells is detected, the detected amount of expression of FOXB2 gene in the stem cells is compared to a detected amount of the expression of FOXB2 gene in control stem cells that have been confirmed to be in an undifferentiated state, and the stem cells in which the detected amount of expression of FOXB2 gene is greater than the detected amount of expression of FOXB2 gene in the control stem cells are isolated.

9. The method according to claim 8, wherein the detecting of an amount of expression of FOXB2 gene is carried out by detecting an amount of FOXB2 mRNA and the comparing of the detected amount of FOXB2 gene is carried out by comparing the detected amount of FOXB2 mRNA.

10. The method according to claim 9, wherein the FOXB2 mRNA is selected from the group consisting of:
 (1) mRNA having a nucleotide sequence shown in SEQ ID NO: 1 or SEQ ID NO: 34,
 (2) mRNA having a nucleotide sequence which has a sequence homology of 97% or more to the nucleotide sequence shown in SEQ ID NO: 1 or SEQ ID NO: 34,
 (3) mRNA encoding an amino acid sequence shown in SEQ ID NO: 2 or SEQ ID NO: 35,
 (4) mRNA encoding an amino acid sequence in which 1-3 amino acids in the amino acid sequence shown in SEQ ID NO: 2 or SEQ ID NO: 35 are deleted, inserted, substituted, or added, and
 (5) mRNA encoding an amino acid sequence which has a sequence homology of 97% or more to the amino acid sequence shown in SEQ ID NO: 2 or SEQ ID NO: 35.

11. The method according to claim 8, wherein the detecting of an amount of expression of FOXB2 gene is carried out by detecting an amount of FOXB2 protein and the comparing of the detected amount of FOXB2 gene is carried out by comparing the detected amount of FOXB2 protein.

12. The method according to claim 11, wherein the FOXB2 protein is selected from the group consisting of:
 (1) a protein having an amino acid sequence shown in SEQ ID NO: 2 or SEQ ID NO: 35,
 (2) a protein having an amino acid sequence shown in SEQ ID NO: 2 or SEQ ID NO: 35 in which 1-3 amino acids are deleted, inserted, substituted, or added, and
 (3) a protein having an amino acid sequence which has a sequence homology of 97% or more to the amino acid sequence shown in SEQ ID NO: 2 or SEQ ID NO: 35.

13. The method according to claim 8, wherein the undifferentiated stem cells are iPS cells or ES cells.

* * * * *

SEQUENCE LISTING

<160> NUMBER OF SEQ ID NOS: 60

<210> SEQ ID NO 1
<211> LENGTH: 1299
<212> TYPE: DNA
<213> ORGANISM: Homo sapiens
<220> FEATURE:
<221> NAME/KEY: CDS
<222> LOCATION: (1)..(1299)

<400> SEQUENCE: 1

```
atg ccg cgg ccg ggg aag agc tcg tac agc gac caa aaa ccg ccc tac      48
Met Pro Arg Pro Gly Lys Ser Ser Tyr Ser Asp Gln Lys Pro Pro Tyr
1               5                  10                  15 tct tac atc tcg ctg acc gcc atg gca atc cag cac tcg gcc gag aag      96
Ser Tyr Ile Ser Leu Thr Ala Met Ala Ile Gln His Ser Ala Glu Lys
            20                  25                  30 atg ctg ccg ctg agc gac atc tac aag ttc atc atg gag cgc ttc ccc     144
Met Leu Pro Leu Ser Asp Ile Tyr Lys Phe Ile Met Glu Arg Phe Pro
```

-continued

```
               35                  40                  45
tac tac cgc gag cac aca cag cgc tgg cag aac agc ctg cgc cac aac      192
Tyr Tyr Arg Glu His Thr Gln Arg Trp Gln Asn Ser Leu Arg His Asn
         50                  55                  60 ctc tcc ttc aac gac tgc ttc atc aag att ccg cgg agg ccc gac cag      240
Leu Ser Phe Asn Asp Cys Phe Ile Lys Ile Pro Arg Arg Pro Asp Gln
 65                  70                  75                  80 cct ggc aag ggt agc ttc tgg gcg ctg cac ccc gac tgc ggg gac atg      288
Pro Gly Lys Gly Ser Phe Trp Ala Leu His Pro Asp Cys Gly Asp Met
                     85                  90                  95 ttc gag aac ggc agc ttc ctg cgg cgt cgc aag cgc ttc aag gtg ctg      336
Phe Glu Asn Gly Ser Phe Leu Arg Arg Arg Lys Arg Phe Lys Val Leu
                100                 105                 110 cgc gcc gac cat act cac ttg cac gcg gga agc acc aag agc gcg ccg      384
Arg Ala Asp His Thr His Leu His Ala Gly Ser Thr Lys Ser Ala Pro
            115                 120                 125 ggc gcc ggt ccg gga ggg cac ctt cac ccc cat cac cac cac cac ccc      432
Gly Ala Gly Pro Gly Gly His Leu His Pro His His His His His Pro
        130                 135                 140 cac cac cac cat cat cac cac gct gcc gca cac cac cac cat cac cac      480
His His His His His His His Ala Ala Ala His His His His His His
145                 150                 155                 160 cac cca ccc cag ccg ccg ccg ccg ccc ccg ccg ccg cac atg              528
His Pro Pro Gln Pro Pro Pro Pro Pro Pro Pro Pro His Met
                165                 170                 175 gta cac tat ttc cat cag caa ccg cct act gct ccg cag ccg cct ccg      576
Val His Tyr Phe His Gln Gln Pro Pro Thr Ala Pro Gln Pro Pro Pro
                180                 185                 190 cac ctc ccg tca cag ccc ccg cag caa ccg ccc cag cag tcg cag cct      624
His Leu Pro Ser Gln Pro Pro Gln Gln Pro Pro Gln Gln Ser Gln Pro
            195                 200                 205 cag cag ccg tct cac ccc ggc aag atg cag gag gcg gcg gcc gtg gcg      672
Gln Gln Pro Ser His Pro Gly Lys Met Gln Glu Ala Ala Ala Val Ala
        210                 215                 220 gcg gcg gcg gcg gcg gcc gcg gca gcc gcg gtg ggc agc gtg gga cgc      720
Ala Ala Ala Ala Ala Ala Ala Ala Ala Val Gly Ser Val Gly Arg
225                 230                 235                 240 ctg tct cag ttc cca ccc tac ggg ctg ggc tcg gcc gcc gcc gct gcc      768
Leu Ser Gln Phe Pro Pro Tyr Gly Leu Gly Ser Ala Ala Ala Ala Ala
                245                 250                 255 gcc gcg gcc gcg gcg tcc acg tca ggc ttc aag cac ccc ttt gcc att      816
Ala Ala Ala Ala Ala Ser Thr Ser Gly Phe Lys His Pro Phe Ala Ile
                260                 265                 270 gag aac att att ggc cgg gac tac aag ggc gtg ctg cag gct gga ggg      864
Glu Asn Ile Ile Gly Arg Asp Tyr Lys Gly Val Leu Gln Ala Gly Gly
            275                 280                 285 ctg ccc ttg gcg tcc gtc atg cac cac ctg ggc tac ccc gtg ccc ggc      912
Leu Pro Leu Ala Ser Val Met His His Leu Gly Tyr Pro Val Pro Gly
        290                 295                 300 cag ctt ggc aac gtc gtc agc tcc gtg tgg ccg cac gtt ggc gtc atg      960
Gln Leu Gly Asn Val Val Ser Ser Val Trp Pro His Val Gly Val Met
305                 310                 315                 320 gat tcg gtg gcc gcc gcc gcg gcc gcc gca gcc gca gcc gga gtc cct     1008
Asp Ser Val Ala Ala Ala Ala Ala Ala Ala Ala Ala Gly Val Pro
                325                 330                 335 gta ggc ccg gag tat ggg gcc ttc ggg gtc ccg gtc aag tcc ctg tgc     1056
Val Gly Pro Glu Tyr Gly Ala Phe Gly Val Pro Val Lys Ser Leu Cys
                340                 345                 350 cac tcg gca agc cag agc ctg cct gcc atg ccg gtg ccc atc aag ccc     1104
```

```
                His Ser Ala Ser Gln Ser Leu Pro Ala Met Pro Val Pro Ile Lys Pro
                            355                 360                 365 acg cct gcg ctg ccg ccc gtg tcc gcg ctg cag ccg ggg ctc act gtc      1152
Thr Pro Ala Leu Pro Pro Val Ser Ala Leu Gln Pro Gly Leu Thr Val
    370                 375                 380 ccc gcg gct tcg cag cag cct ccg gcg cca tcc acc gtg tgc tcc gcg      1200
Pro Ala Ala Ser Gln Gln Pro Pro Ala Pro Ser Thr Val Cys Ser Ala
385                 390                 395                 400 gcc gcg gcc tcg ccc gtt gcc tct ctg ctg gag ccc aca gcc cct acc      1248
Ala Ala Ala Ser Pro Val Ala Ser Leu Leu Glu Pro Thr Ala Pro Thr
                405                 410                 415 tcg gcc gaa agc aag ggc ggc tcc ttg cac tcg gtg cta gtg cac tcc      1296
Ser Ala Glu Ser Lys Gly Gly Ser Leu His Ser Val Leu Val His Ser
                420                 425                 430 tag                                                                   1299

<210> SEQ ID NO 2
<211> LENGTH: 432
<212> TYPE: PRT
<213> ORGANISM: Homo sapiens

<400> SEQUENCE: 2

Met Pro Arg Pro Gly Lys Ser Ser Tyr Ser Asp Gln Lys Pro Pro Tyr
1               5                   10                  15

Ser Tyr Ile Ser Leu Thr Ala Met Ala Ile Gln His Ser Ala Glu Lys
            20                  25                  30

Met Leu Pro Leu Ser Asp Ile Tyr Lys Phe Ile Met Glu Arg Phe Pro
        35                  40                  45

Tyr Tyr Arg Glu His Thr Gln Arg Trp Gln Asn Ser Leu Arg His Asn
    50                  55                  60

Leu Ser Phe Asn Asp Cys Phe Ile Lys Ile Pro Arg Arg Pro Asp Gln
65                  70                  75                  80

Pro Gly Lys Gly Ser Phe Trp Ala Leu His Pro Asp Cys Gly Asp Met
                85                  90                  95

Phe Glu Asn Gly Ser Phe Leu Arg Arg Arg Lys Arg Phe Lys Val Leu
            100                 105                 110

Arg Ala Asp His Thr His Leu His Ala Gly Ser Thr Lys Ser Ala Pro
        115                 120                 125

Gly Ala Gly Pro Gly Gly His Leu His Pro His His His His Pro
    130                 135                 140

His His His His His His Ala Ala Ala His His His His His His
145                 150                 155                 160

His Pro Pro Gln Pro Pro Pro Pro Pro Pro Pro Pro His Met
                165                 170                 175

Val His Tyr Phe His Gln Gln Pro Thr Ala Pro Gln Pro Pro Pro
            180                 185                 190

His Leu Pro Ser Gln Pro Pro Gln Gln Pro Gln Gln Ser Gln Pro
        195                 200                 205

Gln Gln Pro Ser His Pro Gly Lys Met Gln Glu Ala Ala Val Ala
    210                 215                 220

Ala Ala Ala Ala Ala Ala Ala Ala Val Gly Ser Val Gly Arg
225                 230                 235                 240

Leu Ser Gln Phe Pro Pro Tyr Gly Leu Gly Ser Ala Ala Ala Ala
                245                 250                 255

Ala Ala Ala Ala Ala Ser Thr Ser Gly Phe Lys His Pro Phe Ala Ile
            260                 265                 270
```

```
Glu Asn Ile Ile Gly Arg Asp Tyr Lys Gly Val Leu Gln Ala Gly Gly
        275                 280                 285

Leu Pro Leu Ala Ser Val Met His His Leu Gly Tyr Pro Val Pro Gly
    290                 295                 300

Gln Leu Gly Asn Val Val Ser Ser Val Trp Pro His Val Gly Val Met
305                 310                 315                 320

Asp Ser Val Ala Ala Ala Ala Ala Ala Ala Ala Ala Gly Val Pro
                325                 330                 335

Val Gly Pro Glu Tyr Gly Ala Phe Gly Val Pro Val Lys Ser Leu Cys
                340                 345                 350

His Ser Ala Ser Gln Ser Leu Pro Ala Met Pro Val Pro Ile Lys Pro
                355                 360                 365

Thr Pro Ala Leu Pro Pro Val Ser Ala Leu Gln Pro Gly Leu Thr Val
        370                 375                 380

Pro Ala Ala Ser Gln Gln Pro Pro Ala Pro Ser Thr Val Cys Ser Ala
385                 390                 395                 400

Ala Ala Ala Ser Pro Val Ala Ser Leu Leu Glu Pro Thr Ala Pro Thr
                405                 410                 415

Ser Ala Glu Ser Lys Gly Gly Ser Leu His Ser Val Leu Val His Ser
                420                 425                 430

<210> SEQ ID NO 3
<211> LENGTH: 179
<212> TYPE: DNA
<213> ORGANISM: Homo sapiens

<400> SEQUENCE: 3
ctactcttac atctcgctga ccgccatggc aatccagcac tcggccgaga agatgctgcc      60
gctgagcgac atctacaagt tcatcatgga gcgcttcccc tactaccgcg agcacacaca     120
gcgctggcag aacagcctgc gccacaacct ctccttcaac gactgcttca tcaagattc     179

<210> SEQ ID NO 4
<211> LENGTH: 19
<212> TYPE: DNA
<213> ORGANISM: Artificial Sequence
<220> FEATURE:
<223> OTHER INFORMATION: Oligonucleotide primer

<400> SEQUENCE: 4
cagaagctac ccttgccag                                                   19

<210> SEQ ID NO 5
<211> LENGTH: 21
<212> TYPE: DNA
<213> ORGANISM: Artificial Sequence
<220> FEATURE:
<223> OTHER INFORMATION: Oligonucleotide primer

<400> SEQUENCE: 5
gttcttgaag ctaagctgca g                                                21

<210> SEQ ID NO 6
<211> LENGTH: 21
<212> TYPE: DNA
<213> ORGANISM: Artificial Sequence
<220> FEATURE:
<223> OTHER INFORMATION: Oligonucleotide primer

<400> SEQUENCE: 6
```
gttctggaac caggtcttca c					21

<210> SEQ ID NO 7
<211> LENGTH: 21
<212> TYPE: DNA
<213> ORGANISM: Artificial Sequence
<220> FEATURE:
<223> OTHER INFORMATION: Oligonucleotide primer

<400> SEQUENCE: 7
gaccacacca tgaaggcatt c					21

<210> SEQ ID NO 8
<211> LENGTH: 21
<212> TYPE: DNA
<213> ORGANISM: Artificial Sequence
<220> FEATURE:
<223> OTHER INFORMATION: Oligonucleotide primer

<400> SEQUENCE: 8
gtctacatgg caactgtgag g					21

<210> SEQ ID NO 9
<211> LENGTH: 23
<212> TYPE: DNA
<213> ORGANISM: Artificial Sequence
<220> FEATURE:
<223> OTHER INFORMATION: Oligonucleotide primer

<400> SEQUENCE: 9
ctactcttac atctcgctga ccg					23

<210> SEQ ID NO 10
<211> LENGTH: 23
<212> TYPE: DNA
<213> ORGANISM: Artificial Sequence
<220> FEATURE:
<223> OTHER INFORMATION: Oligonucleotide primer

<400> SEQUENCE: 10
gaatcttgat gaagcagtcg ttg					23

<210> SEQ ID NO 11
<211> LENGTH: 22
<212> TYPE: DNA
<213> ORGANISM: Artificial Sequence
<220> FEATURE:
<223> OTHER INFORMATION: Oligonucleotide primer

<400> SEQUENCE: 11
cttggagacc tctcagcctg ag					22

<210> SEQ ID NO 12
<211> LENGTH: 21
<212> TYPE: DNA
<213> ORGANISM: Artificial Sequence
<220> FEATURE:
<223> OTHER INFORMATION: Oligonucleotide primer

<400> SEQUENCE: 12
cttcaggagc ttggcaaatt g					21

<210> SEQ ID NO 13
<211> LENGTH: 22
<212> TYPE: DNA
<213> ORGANISM: Artificial Sequence

```
<220> FEATURE:
<223> OTHER INFORMATION: Oligonucleotide primer

<400> SEQUENCE: 13
cacctatgcc tgtgatttgt gg                                            22

<210> SEQ ID NO 14
<211> LENGTH: 23
<212> TYPE: DNA
<213> ORGANISM: Artificial Sequence
<220> FEATURE:
<223> OTHER INFORMATION: Oligonucleotide primer

<400> SEQUENCE: 14
cattgagtac acacagctgg gtg                                           23

<210> SEQ ID NO 15
<211> LENGTH: 24
<212> TYPE: DNA
<213> ORGANISM: Artificial Sequence
<220> FEATURE:
<223> OTHER INFORMATION: Oligonucleotide primer

<400> SEQUENCE: 15
gtatcaggag ttgtcaaggc agag                                          24

<210> SEQ ID NO 16
<211> LENGTH: 22
<212> TYPE: DNA
<213> ORGANISM: Artificial Sequence
<220> FEATURE:
<223> OTHER INFORMATION: Oligonucleotide primer

<400> SEQUENCE: 16
cagctccgtc tccatcatgt tg                                            22

<210> SEQ ID NO 17
<211> LENGTH: 21
<212> TYPE: DNA
<213> ORGANISM: Artificial Sequence
<220> FEATURE:
<223> OTHER INFORMATION: Oligonucleotide primer

<400> SEQUENCE: 17
gtcaccaggg ctgcttttaa c                                             21

<210> SEQ ID NO 18
<211> LENGTH: 21
<212> TYPE: DNA
<213> ORGANISM: Artificial Sequence
<220> FEATURE:
<223> OTHER INFORMATION: Oligonucleotide primer

<400> SEQUENCE: 18
ggcattgctg atgatcttga g                                             21

<210> SEQ ID NO 19
<211> LENGTH: 21
<212> TYPE: DNA
<213> ORGANISM: Artificial Sequence
<220> FEATURE:
<223> OTHER INFORMATION: Oligonucleotide primer

<400> SEQUENCE: 19
ctccctgaac ttgcagtcat c                                             21
```

```
<210> SEQ ID NO 20
<211> LENGTH: 21
<212> TYPE: DNA
<213> ORGANISM: Artificial Sequence
<220> FEATURE:
<223> OTHER INFORMATION: Oligonucleotide primer

<400> SEQUENCE: 20
cctgaggagt ctagcagagt c                                              21

<210> SEQ ID NO 21
<211> LENGTH: 22
<212> TYPE: DNA
<213> ORGANISM: Artificial Sequence
<220> FEATURE:
<223> OTHER INFORMATION: Oligonucleotide primer

<400> SEQUENCE: 21
gattacgcag tgattatgtc cc                                             22

<210> SEQ ID NO 22
<211> LENGTH: 22
<212> TYPE: DNA
<213> ORGANISM: Artificial Sequence
<220> FEATURE:
<223> OTHER INFORMATION: Oligonucleotide primer

<400> SEQUENCE: 22
catcttgacc cgaatacttg ag                                             22

<210> SEQ ID NO 23
<211> LENGTH: 21
<212> TYPE: DNA
<213> ORGANISM: Artificial Sequence
<220> FEATURE:
<223> OTHER INFORMATION: Oligonucleotide primer

<400> SEQUENCE: 23
cccaggagtc tgaggatttc c                                              21

<210> SEQ ID NO 24
<211> LENGTH: 21
<212> TYPE: DNA
<213> ORGANISM: Artificial Sequence
<220> FEATURE:
<223> OTHER INFORMATION: Oligonucleotide primer

<400> SEQUENCE: 24
gcagagcagt ttccagtgga g                                              21

<210> SEQ ID NO 25
<211> LENGTH: 23
<212> TYPE: DNA
<213> ORGANISM: Artificial Sequence
<220> FEATURE:
<223> OTHER INFORMATION: Oligonucleotide primer

<400> SEQUENCE: 25
gtattcctac aatcccctga gac                                            23

<210> SEQ ID NO 26
<211> LENGTH: 22
<212> TYPE: DNA
<213> ORGANISM: Artificial Sequence
<220> FEATURE:
<223> OTHER INFORMATION: Oligonucleotide primer
```

```
<400> SEQUENCE: 26
caaatatcga gtggtgtaca cg                                           22

<210> SEQ ID NO 27
<211> LENGTH: 21
<212> TYPE: DNA
<213> ORGANISM: Artificial Sequence
<220> FEATURE:
<223> OTHER INFORMATION: Oligonucleotide primer

<400> SEQUENCE: 27
gacacttctc agaggacctg g                                            21

<210> SEQ ID NO 28
<211> LENGTH: 22
<212> TYPE: DNA
<213> ORGANISM: Artificial Sequence
<220> FEATURE:
<223> OTHER INFORMATION: Oligonucleotide primer

<400> SEQUENCE: 28
cagctccttc aggcagtgag ag                                           22

<210> SEQ ID NO 29
<211> LENGTH: 21
<212> TYPE: DNA
<213> ORGANISM: Artificial Sequence
<220> FEATURE:
<223> OTHER INFORMATION: Oligonucleotide primer

<400> SEQUENCE: 29
cgggagacgc atagccttgt g                                            21

<210> SEQ ID NO 30
<211> LENGTH: 22
<212> TYPE: DNA
<213> ORGANISM: Artificial Sequence
<220> FEATURE:
<223> OTHER INFORMATION: Oligonucleotide primer

<400> SEQUENCE: 30
gcttgtggac tctacatgaa ac                                           22

<210> SEQ ID NO 31
<211> LENGTH: 23
<212> TYPE: DNA
<213> ORGANISM: Artificial Sequence
<220> FEATURE:
<223> OTHER INFORMATION: Oligonucleotide primer

<400> SEQUENCE: 31
gctgcaatca tctgagttag aag                                          23

<210> SEQ ID NO 32
<211> LENGTH: 21
<212> TYPE: DNA
<213> ORGANISM: Artificial Sequence
<220> FEATURE:
<223> OTHER INFORMATION: Oligonucleotide primer

<400> SEQUENCE: 32
cggaatttga acagtatctg c                                            21

<210> SEQ ID NO 33
```

```
<211> LENGTH: 22
<212> TYPE: DNA
<213> ORGANISM: Artificial Sequence
<220> FEATURE:
<223> OTHER INFORMATION: Oligonucleotide primer

<400> SEQUENCE: 33
gctcctccag gaagtgtgta ac                                              22

<210> SEQ ID NO 34
<211> LENGTH: 1515
<212> TYPE: DNA
<213> ORGANISM: Mus musculus
<220> FEATURE:
<221> NAME/KEY: CDS
<222> LOCATION: (191)..(1474)

<400> SEQUENCE: 34
ttgcggggac ccggggcagc tccccgaagg aggaggacca aggcaaaagg ggtctgggga     60
ccaagaaagc tggggatcag ctggcgcagg tggagagaga attagtgggg acacttaagc   120
ctggtatccg gctttccaag aggcgttaag gcccactgtg ggccggacgg aggtggaaga   180
gcctgggaag atg cca cgg cca ggg aag agt tcc tac agc gac caa aag      229
            Met Pro Arg Pro Gly Lys Ser Ser Tyr Ser Asp Gln Lys
              1               5                  10 ccg ccc tac tct tac atc tca ctg acc gcc atg gcc atc cag cat tcg    277
Pro Pro Tyr Ser Tyr Ile Ser Leu Thr Ala Met Ala Ile Gln His Ser
     15                  20                  25 gct gag aag atg ctg cct ctg agc gac atc tac aag ttc atc atg gag    325
Ala Glu Lys Met Leu Pro Leu Ser Asp Ile Tyr Lys Phe Ile Met Glu
 30                  35                  40                  45 cgc ttc ccc tac tac cgc gag cac acg cag cgc tgg cag aac agc ctg    373
Arg Phe Pro Tyr Tyr Arg Glu His Thr Gln Arg Trp Gln Asn Ser Leu
                 50                  55                  60 cgc cac aac ctc tcc ttc aac gac tgt ttc atc aag atc cct cgg agg    421
Arg His Asn Leu Ser Phe Asn Asp Cys Phe Ile Lys Ile Pro Arg Arg
             65                  70                  75 ccg gac caa ccc ggt aag ggc agc ttc tgg gcg cta cac cct gac tgc    469
Pro Asp Gln Pro Gly Lys Gly Ser Phe Trp Ala Leu His Pro Asp Cys
         80                  85                  90 ggt gac atg ttc gag aac ggc agc ttc ctg cgg cgc cgc aag cgc ttc    517
Gly Asp Met Phe Glu Asn Gly Ser Phe Leu Arg Arg Arg Lys Arg Phe
     95                 100                 105 aag gtg cta cgc gca gac cac gct cac cta cac tca gga agc agc aag    565
Lys Val Leu Arg Ala Asp His Ala His Leu His Ser Gly Ser Ser Lys
110                 115                 120                 125 ggc gcg ccc ggc acg ggg cca gga ggt cac ctg cat ccc cac cat ccc    613
Gly Ala Pro Gly Thr Gly Pro Gly Gly His Leu His Pro His His Pro
                130                 135                 140 cac cac gca cac cac cac cac cat cac cac cac gcc gca cac cat        661
His His Ala His His His His His His His His His Ala Ala His His
                145                 150                 155 cac cac cat cac cac ccg ccg cag ccg ccc ccg ccg ccg ccg cac        709
His His His His His Pro Pro Gln Pro Pro Pro Pro Pro Pro His
                160                 165                 170 atg gtg ccc tat ttc cac cag cag ccg gct ccg gct ccg cag cct cca    757
Met Val Pro Tyr Phe His Gln Gln Pro Ala Pro Ala Pro Gln Pro Pro
    175                 180                 185 cac ctc ccg tcg cag ccc gcg cag cag cca cag ccg cag tcg cag cct    805
His Leu Pro Ser Gln Pro Ala Gln Gln Pro Gln Pro Gln Ser Gln Pro
190                 195                 200                 205
```

| | | | | | | | | | | | | | | | | |
|---|---|---|---|---|---|---|---|---|---|---|---|---|---|---|---|---|
| ccg | cag | acg | tcc | cat | ccc | ggc | aag | atg | cag | gag | gcg | gcg | gcc | gtg | gcg | 853 |
| Pro | Gln | Thr | Ser | His | Pro | Gly | Lys | Met | Gln | Glu | Ala | Ala | Ala | Val | Ala | |
| | | | | 210 | | | | 215 | | | | 220 | | | | |
| gcg | gcc | gca | gca | gcg | gcg | gcc | gca | gcg | gtg | ggc | agc | gtg | ggg | cgt | | 901 |
| Ala | Ala | Ala | Ala | Ala | Ala | Ala | Ala | Ala | Val | Gly | Ser | Val | Gly | Arg | | |
| | | 225 | | | | | 230 | | | | | 235 | | | | |
| ctg | tct | cag | ttc | cca | ccc | tac | ggg | ctg | ggc | tcg | gcc | gcc | gcc | gcc | gcc | 949 |
| Leu | Ser | Gln | Phe | Pro | Pro | Tyr | Gly | Leu | Gly | Ser | Ala | Ala | Ala | Ala | Ala | |
| | | | 240 | | | | 245 | | | | | 250 | | | | |
| gct | gca | gcc | gcc | gcg | tcc | acc | aca | ggc | ttc | aaa | cat | ccg | ttc | gcc | ata | 997 |
| Ala | Ala | Ala | Ala | Ala | Ser | Thr | Thr | Gly | Phe | Lys | His | Pro | Phe | Ala | Ile | |
| | 255 | | | | | 260 | | | | | 265 | | | | | |
| gag | aac | atc | atc | ggg | cgg | gac | tac | aag | ggc | gtg | ctg | cag | gct | gga | ggg | 1045 |
| Glu | Asn | Ile | Ile | Gly | Arg | Asp | Tyr | Lys | Gly | Val | Leu | Gln | Ala | Gly | Gly | |
| 270 | | | | | 275 | | | | | 280 | | | | | 285 | |
| ttg | cct | ttg | gcg | tcg | gtc | atg | cac | cac | ttg | ggc | tac | ccc | gtg | ccg | ggc | 1093 |
| Leu | Pro | Leu | Ala | Ser | Val | Met | His | His | Leu | Gly | Tyr | Pro | Val | Pro | Gly | |
| | | | | 290 | | | | 295 | | | | 300 | | | | |
| cag | ctc | agc | aat | gtt | gtc | ggc | tcc | gtg | tgg | cct | cat | gtt | ggc | gtg | atg | 1141 |
| Gln | Leu | Ser | Asn | Val | Val | Gly | Ser | Val | Trp | Pro | His | Val | Gly | Val | Met | |
| | | | 305 | | | | 310 | | | | | 315 | | | | |
| gat | tcg | gta | gcc | gcg | gct | gcc | gct | gct | gcc | gcc | gca | gct | ggg | gtc | ccg | 1189 |
| Asp | Ser | Val | Ala | Ala | Ala | Ala | Ala | Ala | Ala | Ala | Ala | Ala | Gly | Val | Pro | |
| | | 320 | | | | | 325 | | | | | 330 | | | | |
| gta | ggc | ccg | gag | tat | ggg | gca | ttc | ggg | gtg | cca | gtc | aag | gct | ctg | tgc | 1237 |
| Val | Gly | Pro | Glu | Tyr | Gly | Ala | Phe | Gly | Val | Pro | Val | Lys | Ala | Leu | Cys | |
| | | 335 | | | | | 340 | | | | | 345 | | | | |
| cac | tcg | gca | aac | cag | agc | ctg | cca | gct | gta | ccg | gtg | ccc | atc | aag | ccc | 1285 |
| His | Ser | Ala | Asn | Gln | Ser | Leu | Pro | Ala | Val | Pro | Val | Pro | Ile | Lys | Pro | |
| 350 | | | | | 355 | | | | | 360 | | | | | 365 | |
| acg | cct | gcg | cta | cca | ccc | gtg | acc | acg | ctg | ccg | ccg | gcg | ttg | tct | gtc | 1333 |
| Thr | Pro | Ala | Leu | Pro | Pro | Val | Thr | Thr | Leu | Pro | Pro | Ala | Leu | Ser | Val | |
| | | | | 370 | | | | 375 | | | | | 380 | | | |
| ccc | acg | gcg | tcg | cag | cag | ctg | cct | gct | ccc | tcc | acc | gtg | tgc | gcg | gcc | 1381 |
| Pro | Thr | Ala | Ser | Gln | Gln | Leu | Pro | Ala | Pro | Ser | Thr | Val | Cys | Ala | Ala | |
| | | | 385 | | | | 390 | | | | | 395 | | | | |
| gcc | gcc | tca | ccc | aca | gcc | cct | ctc | ttg | gag | ccc | acc | gca | gcc | ggc | agg | 1429 |
| Ala | Ala | Ser | Pro | Thr | Ala | Pro | Leu | Leu | Glu | Pro | Thr | Ala | Ala | Gly | Arg | |
| | | 400 | | | | 405 | | | | | 410 | | | | | |
| gct | gac | agc | aag | ggg | agc | tcc | cta | cac | tcg | gtg | ttg | gtg | cat | tct | | 1474 |
| Ala | Asp | Ser | Lys | Gly | Ser | Ser | Leu | His | Ser | Val | Leu | Val | His | Ser | | |
| | 415 | | | | 420 | | | | | 425 | | | | | | |
| tagggaccc cgcgaccggt gagaaggcgc ctgtcgagag a | | | | | | | | | | | | | | | | 1515 |

<210> SEQ ID NO 35
<211> LENGTH: 428
<212> TYPE: PRT
<213> ORGANISM: Mus musculus

<400> SEQUENCE: 35

Met Pro Arg Pro Gly Lys Ser Ser Tyr Ser Asp Gln Lys Pro Pro Tyr
1               5                   10                  15

Ser Tyr Ile Ser Leu Thr Ala Met Ala Ile Gln His Ser Ala Glu Lys
            20                  25                  30

Met Leu Pro Leu Ser Asp Ile Tyr Lys Phe Ile Met Glu Arg Phe Pro
        35                  40                  45

Tyr Tyr Arg Glu His Thr Gln Arg Trp Gln Asn Ser Leu Arg His Asn
    50                  55                  60

Leu Ser Phe Asn Asp Cys Phe Ile Lys Ile Pro Arg Arg Pro Asp Gln

-continued

```
                65                  70                  75                  80
Pro Gly Lys Gly Ser Phe Trp Ala Leu His Pro Asp Cys Gly Asp Met
                    85                  90                  95

Phe Glu Asn Gly Ser Phe Leu Arg Arg Arg Lys Arg Phe Lys Val Leu
                100                 105                 110

Arg Ala Asp His Ala His Leu His Ser Gly Ser Ser Lys Gly Ala Pro
            115                 120                 125

Gly Thr Gly Pro Gly Gly His Leu His Pro His His Pro His His Ala
        130                 135                 140

His His His His His His His His Ala Ala His His His His His His
145                 150                 155                 160

His His Pro Pro Gln Pro Pro Pro Pro Pro His Met Val Pro
                165                 170                 175

Tyr Phe His Gln Gln Pro Ala Pro Ala Pro Gln Pro Pro His Leu Pro
                180                 185                 190

Ser Gln Pro Ala Gln Gln Pro Gln Pro Gln Ser Gln Pro Pro Gln Thr
            195                 200                 205

Ser His Pro Gly Lys Met Gln Glu Ala Ala Ala Val Ala Ala Ala Ala
        210                 215                 220

Ala Ala Ala Ala Ala Ala Val Gly Ser Val Gly Arg Leu Ser Gln
225                 230                 235                 240

Phe Pro Pro Tyr Gly Leu Gly Ser Ala Ala Ala Ala Ala Ala Ala
                245                 250                 255

Ala Ala Ser Thr Thr Gly Phe Lys His Pro Phe Ala Ile Glu Asn Ile
                260                 265                 270

Ile Gly Arg Asp Tyr Lys Gly Val Leu Gln Ala Gly Gly Leu Pro Leu
        275                 280                 285

Ala Ser Val Met His His Leu Gly Tyr Pro Val Pro Gly Gln Leu Ser
        290                 295                 300

Asn Val Val Gly Ser Val Trp Pro His Val Gly Val Met Asp Ser Val
305                 310                 315                 320

Ala Ala Ala Ala Ala Ala Ala Ala Gly Val Pro Val Gly Pro
                325                 330                 335

Glu Tyr Gly Ala Phe Gly Val Pro Val Lys Ala Leu Cys His Ser Ala
                340                 345                 350

Asn Gln Ser Leu Pro Ala Val Pro Val Pro Ile Lys Pro Thr Pro Ala
            355                 360                 365

Leu Pro Pro Val Thr Thr Leu Pro Pro Ala Leu Ser Val Pro Thr Ala
        370                 375                 380

Ser Gln Gln Leu Pro Ala Pro Ser Thr Val Cys Ala Ala Ala Ser
385                 390                 395                 400

Pro Thr Ala Pro Leu Leu Glu Pro Thr Ala Ala Gly Arg Ala Asp Ser
                405                 410                 415

Lys Gly Ser Ser Leu His Ser Val Leu Val His Ser
            420                 425

<210> SEQ ID NO 36
<211> LENGTH: 169
<212> TYPE: DNA
<213> ORGANISM: Mus musculus

<400> SEQUENCE: 36
ctttccaaga ggcgttaagg cccactgtgg gccggacgga ggtggaagag cctgggaaga      60
tgccacggcc agggaagagt tcctacagcg accaaaagcc gccctactct tacatctcac     120
```
tgaccgccat ggccatccag cattcggctg agaagatgct gcctctgag    169

<210> SEQ ID NO 37
<211> LENGTH: 21
<212> TYPE: DNA
<213> ORGANISM: Artificial Sequence
<220> FEATURE:
<223> OTHER INFORMATION: Oligonucleotide primer

<400> SEQUENCE: 37
catgatgaac ttgtagatgt c    21

<210> SEQ ID NO 38
<211> LENGTH: 22
<212> TYPE: DNA
<213> ORGANISM: Artificial Sequence
<220> FEATURE:
<223> OTHER INFORMATION: Oligonucleotide primer

<400> SEQUENCE: 38
catgttctta aggctgagct gc    22

<210> SEQ ID NO 39
<211> LENGTH: 22
<212> TYPE: DNA
<213> ORGANISM: Artificial Sequence
<220> FEATURE:
<223> OTHER INFORMATION: Oligonucleotide primer

<400> SEQUENCE: 39
ctgaatcaga ccattgctag tc    22

<210> SEQ ID NO 40
<211> LENGTH: 21
<212> TYPE: DNA
<213> ORGANISM: Artificial Sequence
<220> FEATURE:
<223> OTHER INFORMATION: Oligonucleotide primer

<400> SEQUENCE: 40
caacgatatc aacctgcatg g    21

<210> SEQ ID NO 41
<211> LENGTH: 23
<212> TYPE: DNA
<213> ORGANISM: Artificial Sequence
<220> FEATURE:
<223> OTHER INFORMATION: Oligonucleotide primer

<400> SEQUENCE: 41
gaactggtgg cagagtcatt ttc    23

<210> SEQ ID NO 42
<211> LENGTH: 24
<212> TYPE: DNA
<213> ORGANISM: Artificial Sequence
<220> FEATURE:
<223> OTHER INFORMATION: Oligonucleotide primer

<400> SEQUENCE: 42
gattcgagac gatcttagtc aatg    24

<210> SEQ ID NO 43
<211> LENGTH: 21
<212> TYPE: DNA

```
<213> ORGANISM: Artificial Sequence
<220> FEATURE:
<223> OTHER INFORMATION: Oligonucleotide primer

<400> SEQUENCE: 43
gacgcatagg tattatagct g                                              21

<210> SEQ ID NO 44
<211> LENGTH: 21
<212> TYPE: DNA
<213> ORGANISM: Artificial Sequence
<220> FEATURE:
<223> OTHER INFORMATION: Oligonucleotide primer

<400> SEQUENCE: 44
cttgatgtca tcatacttgg c                                              21

<210> SEQ ID NO 45
<211> LENGTH: 21
<212> TYPE: DNA
<213> ORGANISM: Artificial Sequence
<220> FEATURE:
<223> OTHER INFORMATION: Oligonucleotide primer

<400> SEQUENCE: 45
ctttccaaga ggcgttaagg c                                              21

<210> SEQ ID NO 46
<211> LENGTH: 22
<212> TYPE: DNA
<213> ORGANISM: Artificial Sequence
<220> FEATURE:
<223> OTHER INFORMATION: Oligonucleotide primer

<400> SEQUENCE: 46
ctcagaggca gcatcttctc ag                                             22

<210> SEQ ID NO 47
<211> LENGTH: 21
<212> TYPE: DNA
<213> ORGANISM: Artificial Sequence
<220> FEATURE:
<223> OTHER INFORMATION: Oligonucleotide primer

<400> SEQUENCE: 47
gaacctggct aagcttccaa g                                              21

<210> SEQ ID NO 48
<211> LENGTH: 22
<212> TYPE: DNA
<213> ORGANISM: Artificial Sequence
<220> FEATURE:
<223> OTHER INFORMATION: Oligonucleotide primer

<400> SEQUENCE: 48
gcttggcaaa ctgttctagc tc                                             22

<210> SEQ ID NO 49
<211> LENGTH: 25
<212> TYPE: DNA
<213> ORGANISM: Artificial Sequence
<220> FEATURE:
<223> OTHER INFORMATION: Oligonucleotide primer

<400> SEQUENCE: 49
gcattagaca tttaactctt ctttc                                          25
```

<210> SEQ ID NO 50
<211> LENGTH: 21
<212> TYPE: DNA
<213> ORGANISM: Artificial Sequence
<220> FEATURE:
<223> OTHER INFORMATION: Oligonucleotide primer

<400> SEQUENCE: 50
cttgaagagg caggtcttca g                                              21

<210> SEQ ID NO 51
<211> LENGTH: 23
<212> TYPE: DNA
<213> ORGANISM: Artificial Sequence
<220> FEATURE:
<223> OTHER INFORMATION: Oligonucleotide primer

<400> SEQUENCE: 51
gaatcggacc atgtatagat ctg                                            23

<210> SEQ ID NO 52
<211> LENGTH: 24
<212> TYPE: DNA
<213> ORGANISM: Artificial Sequence
<220> FEATURE:
<223> OTHER INFORMATION: Oligonucleotide primer

<400> SEQUENCE: 52
catttgattg ccatgtttat ctcg                                           24

<210> SEQ ID NO 53
<211> LENGTH: 22
<212> TYPE: DNA
<213> ORGANISM: Artificial Sequence
<220> FEATURE:
<223> OTHER INFORMATION: Oligonucleotide primer

<400> SEQUENCE: 53
gaagccttat cattgcaact gg                                             22

<210> SEQ ID NO 54
<211> LENGTH: 24
<212> TYPE: DNA
<213> ORGANISM: Artificial Sequence
<220> FEATURE:
<223> OTHER INFORMATION: Oligonucleotide primer

<400> SEQUENCE: 54
ctgtcctaag gtccaataaa tagc                                           24

<210> SEQ ID NO 55
<211> LENGTH: 22
<212> TYPE: DNA
<213> ORGANISM: Artificial Sequence
<220> FEATURE:
<223> OTHER INFORMATION: Oligonucleotide primer

<400> SEQUENCE: 55
gcaagagcta cgaggactgt ac                                             22

<210> SEQ ID NO 56
<211> LENGTH: 23
<212> TYPE: DNA
<213> ORGANISM: Artificial Sequence
<220> FEATURE:

```
<223> OTHER INFORMATION: Oligonucleotide primer

<400> SEQUENCE: 56
gtttggtgat ctcacattca ttg                                               23

<210> SEQ ID NO 57
<211> LENGTH: 21
<212> TYPE: DNA
<213> ORGANISM: Artificial Sequence
<220> FEATURE:
<223> OTHER INFORMATION: Oligonucleotide primer

<400> SEQUENCE: 57
gaacatagca gtttccagtg g                                                 21

<210> SEQ ID NO 58
<211> LENGTH: 23
<212> TYPE: DNA
<213> ORGANISM: Artificial Sequence
<220> FEATURE:
<223> OTHER INFORMATION: Oligonucleotide primer

<400> SEQUENCE: 58
gttgctgaaa actcctcgta ttc                                               23

<210> SEQ ID NO 59
<211> LENGTH: 23
<212> TYPE: DNA
<213> ORGANISM: Artificial Sequence
<220> FEATURE:
<223> OTHER INFORMATION: Oligonucleotide primer

<400> SEQUENCE: 59
gttccagtat gactccactc acg                                               23

<210> SEQ ID NO 60
<211> LENGTH: 23
<212> TYPE: DNA
<213> ORGANISM: Artificial Sequence
<220> FEATURE:
<223> OTHER INFORMATION: Oligonucleotide primer

<400> SEQUENCE: 60
cattgctgac aatcttgagt gag                                               23
```